(12) United States Patent
Davi et al.

(10) Patent No.: US 7,416,851 B2
(45) Date of Patent: Aug. 26, 2008

(54) METHOD OF DIAGNOSIS/PROGNOSIS OF HUMAN CHRONIC LYMPHOCYTIC LEUKEMIA COMPRISING THE PROFILING OF LPL/ADAM GENES

(75) Inventors: Frederic Davi, Meudon (FR); Guillaume Dighiero, Paris (FR); Gerard Dumas, Juziers (FR); Pablo Oppezzo, Paris (FR); Catherine Settegrana, Antony (FR); Yuri Vasconcelos Pinheiro, Goiania-Goias (BR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 10/982,908

(22) Filed: Nov. 8, 2004

(65) Prior Publication Data
US 2006/0099603 A1     May 11, 2006

(51) Int. Cl.
*C12Q 1/68*     (2006.01)
(52) U.S. Cl. .......................................... 435/7.23; 435/6
(58) Field of Classification Search ............... 435/6, 435/7.1, 7.2, 7.21, 7.23
See application file for complete search history.

(56) References Cited

U.S. PATENT DOCUMENTS
2006/0099603 A1    5/2006    Davi et al.

OTHER PUBLICATIONS

Guo et al., J Pharmacology and Experimemtal Therapeutics, 2002, 300(1): 206-212.*
Vallejo Biochimie, 2000, 82:1129-1133.*
Tockman et al, Cancer Research, 1992, 52:2711s-2718s.*
Carrere, Gut, 1999, 44:545-551.*
Alberts et al., Molecular Biology of the cell, 3rd Ed 1994, p. 465.*
Lewin, Genes VI, Oxford University Press, NY, Chapter 29, 1997, p. 847-848.*
Fu et al, EMBO Journal, 1996, 15:4392-4401.*
Mallampalli et al., Biochem J, 1996, 318:333-341.*
Shantz and Pegg, 1999, Int J Biochem Cell Biol., 31:107-122.*
McClean and Hill, Eur J Cancer, 1993, 29:2243-2248.*
Greenbaum et al, Genome Biol, 2003, 4(9): 117.1-117.8.*
Brennan et al, J Autoimmunity, 1989, 2:177-186.*
Eriksson et al, Diabetologia, 1992, 35:143-147.*
Hell et al, Laboratory Investigation, 1995, 73:492-496.*
Powel, Pharmacogenesis, 1998, 8:411-421.*
Klein et al. (J. Exp. Med. 2001; 194: 1625-1638).*
(Cerretti et al., Biochemical and Biophysical Reasearch Communications 1999; 263, 810-815).*
Tockman et al (Cancer Res., 1992, 52:2711s-2718s).*
Slamon et al. (Science vol. 235, Jan. 1987, pp. 177-182).*
National Cancer Institute,"Understanding Prognosis and Cancer Statistics", Dec. 2003.*
Montesserrat (Hematology 2006; 279-284).*
Guillaume Dighiero, "Unsolved issues in CLL biology and management", Leukemia, vol. 17, 2003, pp. 2385-2391.
Douglas Pat Cerretti, et al., "Isolation of Two Novel Metalloproteinase-Disintegrin (ADAM) cDNAs That Show Testis-Specific Gene Expression", Biochemical and Biophysical Research Communications, vol. 263, No. 3, 1999, pp. 810-815.
Rener Xu, et al., "Molecular Cloning and Mapping of a Novel ADAM Gene (ADAM29) to Human Chromosome 4", Genomics, vol. 62, 1999, pp. 537-539.
Atsuko Takagi, et al., "DNA sequence of lipoprotein lipase cDNA cloned from human monocytic leukemia THP-1 cells", Nucleic Acids Research, vol. 18, No. 21, 1990, 1 page.
Yuri Vasconcelos, et al., "Combination of LPL/ADAM29 Ratio and Zap-70 Expression Can Dispense IgVH Sequencing in CLL", American Society of Hematology, 45th Annual meeting and exposition, Dec. 6-9, 2003, 1 page.
Pablo Oppezzo, et al., "The LPL/ADAM29 expression ratio is a novel prognosis indicator in chronic lymphocytic leukemia", Blood First Edition Paper, prepublished online Mar. 31, 2005, pp. 1-31.
E. Beillard, et al., "Evaluation of candidate control genes for diagnosis and residual disease detection in leukemic patients using 'real-time' quantitative reverse-transcriptase polymerase chain reaction (RQ-PCR)—a Europe against cancer program", Leukemia, vol. 17, 2003, pp. 2474-2486.
U.S. Appl. No. 11/718,837, filed May 8, 2007, Davi et al.

* cited by examiner

*Primary Examiner*—Brandon Fetterolf
(74) *Attorney, Agent, or Firm*—Oblon, Spivak, McClelland, Maier & Neustadt, P.C.

(57) ABSTRACT

The present invention provides methods of diagnosis and prognosis of human chronic lymphocytic leukemia (CLL) in a subject a patient in need thereof. The methods of the present invention involve measuring the expression profile of two known genes: LPL and ADAM29; and comparing the ratio of their expression to diagnose the presence of CLL or to prognose the likelihood of developing CLL or the symptoms consistent with CLL.

6 Claims, 4 Drawing Sheets

```
                            SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
ggtgctgagt atgtcgtgga                                                      20

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA

<400> SEQUENCE: 2
atgccagtga gcttccgtt                                                       19

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
ggaatgtatg agagttgggt gc                                                   22

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
caatgcttcg accaggggac c                                                    21
```

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA

<400> SEQUENCE: 5
tcttatgtgg gctggtggat cc                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA

<400> SEQUENCE: 6
gacctagatg atgagccact gc                                              22

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7
ctgaaatgta ctgcgggagc c                                               21

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA

<400> SEQUENCE: 8
ccaactcacc caggaagcac c                                               21

<210> SEQ ID NO 9
<211> LENGTH: 22
<212> TYPE: DNA
<213> ORGANISM: Artificial Sequence
<220> FEATURE:
<223> OTHER INFORMATION: Synthetic DNA

<400> SEQUENCE: 9
ggatagcaca ttactggcct ct                                              22

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
aggtttaggt gaggtggcag g                                               21

<210> SEQ ID NO 11
<211> LENGTH: 1428
<212> TYPE: DNA
<213> ORGANISM: Homo sapiens
<220> FEATURE:
<221> NAME/KEY: CDS

<222> LOCATION: (1)..(1428)

<400> SEQUENCE: 11

```
atg gag agc aaa gcc ctg ctc gtg ctg act ctg gcc gtg tgg ctc cag      48
Met Glu Ser Lys Ala Leu Leu Val Leu Thr Leu Ala Val Trp Leu Gln
1               5                   10                  15 agt ctg acc gcc tcc cgc gga ggg gtg gcc gcc gcc gac caa aga aga      96
Ser Leu Thr Ala Ser Arg Gly Gly Val Ala Ala Ala Asp Gln Arg Arg
            20                  25                  30 gat ttt atc gac atc gaa agt aaa ttt gcc cta agg acc cct gaa gac     144
Asp Phe Ile Asp Ile Glu Ser Lys Phe Ala Leu Arg Thr Pro Glu Asp
        35                  40                  45 aca gct gag gac act tgc cac ctc att ccc gga gta gca gag tcc gtg     192
Thr Ala Glu Asp Thr Cys His Leu Ile Pro Gly Val Ala Glu Ser Val
    50                  55                  60 gct acc tgt cat ttc aat cac agc agc aaa acc ttc atg gtg atc cat     240
Ala Thr Cys His Phe Asn His Ser Ser Lys Thr Phe Met Val Ile His
65                  70                  75                  80 ggc tgg acg gta aca gga atg tat gag agt tgg gtg cca aaa ctt gtg     288
Gly Trp Thr Val Thr Gly Met Tyr Glu Ser Trp Val Pro Lys Leu Val
                85                  90                  95 gcc gcc ctg tac aag aga gaa cca gac tcc aat gtc att gtg gtg gac     336
Ala Ala Leu Tyr Lys Arg Glu Pro Asp Ser Asn Val Ile Val Val Asp
            100                 105                 110 tgg ctg tca cgg gct cag gag cat tac cca gtg tcc gcg ggc tac acc     384
Trp Leu Ser Arg Ala Gln Glu His Tyr Pro Val Ser Ala Gly Tyr Thr
        115                 120                 125 aaa ctg gtg gga cag gat gtg gcc cgg ttt atc aac tgg atg gag gag     432
Lys Leu Val Gly Gln Asp Val Ala Arg Phe Ile Asn Trp Met Glu Glu
    130                 135                 140 gag ttt aac tac cct ctg gac aat gtc cat ctc ttg gga tac agc ctt     480
Glu Phe Asn Tyr Pro Leu Asp Asn Val His Leu Leu Gly Tyr Ser Leu
145                 150                 155                 160 gga gcc cat gct gct ggc att gca gga agt ctg acc aat aag aaa gtc     528
Gly Ala His Ala Ala Gly Ile Ala Gly Ser Leu Thr Asn Lys Lys Val
                165                 170                 175 aac aga att act ggc ctc gat cca gct gga cct aac ttt gag tat gca     576
Asn Arg Ile Thr Gly Leu Asp Pro Ala Gly Pro Asn Phe Glu Tyr Ala
            180                 185                 190 gaa gcc ccg agt cgt ctt tct cct gat gat gca gat ttt gta gac gtc     624
Glu Ala Pro Ser Arg Leu Ser Pro Asp Asp Ala Asp Phe Val Asp Val
        195                 200                 205 tta cac aca ttc acc aga ggg tcc cct ggt cga agc att gga atc cag     672
Leu His Thr Phe Thr Arg Gly Ser Pro Gly Arg Ser Ile Gly Ile Gln
    210                 215                 220 aaa cca gtt ggg cat gtt gac att tac ccg aat gga ggt act ttt cag     720
Lys Pro Val Gly His Val Asp Ile Tyr Pro Asn Gly Gly Thr Phe Gln
225                 230                 235                 240 cca gga tgt aac att gga gaa gct atc cgc gtg att gca gag aga gga     768
Pro Gly Cys Asn Ile Gly Glu Ala Ile Arg Val Ile Ala Glu Arg Gly
                245                 250                 255 ctt gga gat gtg gac cag cta gtg aag tgc tcc cac gag cgc tcc att     816
Leu Gly Asp Val Asp Gln Leu Val Lys Cys Ser His Glu Arg Ser Ile
            260                 265                 270 cat ctc ttc atc gac tct ctg ttg aat gaa gaa aat cca agt aag gcc     864
His Leu Phe Ile Asp Ser Leu Leu Asn Glu Glu Asn Pro Ser Lys Ala
        275                 280                 285 tac agg tgc agt tcc aag gaa gcc ttt gag aaa ggg ctc tgc ttg agt     912
Tyr Arg Cys Ser Ser Lys Glu Ala Phe Glu Lys Gly Leu Cys Leu Ser
    290                 295                 300
```

```
tgt aga aag aac cgc tgc aac aat ctg ggc tat gag atc agt aaa gtc        960
Cys Arg Lys Asn Arg Cys Asn Asn Leu Gly Tyr Glu Ile Ser Lys Val
305                 310                 315                 320 aga gcc aaa aga agc agc aaa atg tac ctg aag act cgt tct cag atg       1008
Arg Ala Lys Arg Ser Ser Lys Met Tyr Leu Lys Thr Arg Ser Gln Met
                325                 330                 335 ccc tac aaa gtc ttc cat tac caa gta aag att cat ttt tct ggg act       1056
Pro Tyr Lys Val Phe His Tyr Gln Val Lys Ile His Phe Ser Gly Thr
            340                 345                 350 gag agt gaa acc cat acc aat cag gcc ttt gag att tct ctg tat ggc       1104
Glu Ser Glu Thr His Thr Asn Gln Ala Phe Glu Ile Ser Leu Tyr Gly
        355                 360                 365 acc gtg gcc gag agt gag aac atc cca ttc act ctg cct gaa gtt tcc       1152
Thr Val Ala Glu Ser Glu Asn Ile Pro Phe Thr Leu Pro Glu Val Ser
    370                 375                 380 aca aat aag acc tac tcc ttc cta att tac aca gag gta gat att gga       1200
Thr Asn Lys Thr Tyr Ser Phe Leu Ile Tyr Thr Glu Val Asp Ile Gly
385                 390                 395                 400 gaa cta ctc atg ttg aag ctc aaa tgg aag agt gat tca tac ttt agc       1248
Glu Leu Leu Met Leu Lys Leu Lys Trp Lys Ser Asp Ser Tyr Phe Ser
                405                 410                 415 tgg tca gac tgg tgg agc agt ccc ggc ttc gcc att cag aag atc aga       1296
Trp Ser Asp Trp Trp Ser Ser Pro Gly Phe Ala Ile Gln Lys Ile Arg
                420                 425                 430 gta aaa gca gga gag act cag aaa aag gtg atc ttc tgt tct agg gag       1344
Val Lys Ala Gly Glu Thr Gln Lys Lys Val Ile Phe Cys Ser Arg Glu
            435                 440                 445 aaa gtg tct cat ttg cag aaa gga aag gca cct gcg gta ttt gtg aaa       1392
Lys Val Ser His Leu Gln Lys Gly Lys Ala Pro Ala Val Phe Val Lys
        450                 455                 460 tgc cat gac aag tct ctg aat aag aag tca ggc tag                       1428
Cys His Asp Lys Ser Leu Asn Lys Lys Ser Gly
465                 470                 475

<210> SEQ ID NO 12
<211> LENGTH: 475
<212> TYPE: PRT
<213> ORGANISM: Homo sapiens

<400> SEQUENCE: 12

Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
        35                  40                  45

Thr Ala Glu Asp Thr Cys His Leu Ile Pro Gly Val Ala Glu Ser Val
    50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
        115                 120                 125

Lys Leu Val Gly Gln Asp Val Ala Arg Phe Ile Asn Trp Met Glu Glu
    130                 135                 140
```

```
Glu Phe Asn Tyr Pro Leu Asp Asn Val His Leu Leu Gly Tyr Ser Leu
145                 150                 155                 160
Gly Ala His Ala Ala Gly Ile Ala Gly Ser Leu Thr Asn Lys Lys Val
            165                 170                 175
Asn Arg Ile Thr Gly Leu Asp Pro Ala Gly Pro Asn Phe Glu Tyr Ala
        180                 185                 190
Glu Ala Pro Ser Arg Leu Ser Pro Asp Ala Asp Phe Val Asp Val
            195                 200                 205
Leu His Thr Phe Thr Arg Gly Ser Pro Gly Arg Ser Ile Gly Ile Gln
210                 215                 220
Lys Pro Val Gly His Val Asp Ile Tyr Pro Asn Gly Gly Thr Phe Gln
225                 230                 235                 240
Pro Gly Cys Asn Ile Gly Glu Ala Ile Arg Val Ile Ala Glu Arg Gly
            245                 250                 255
Leu Gly Asp Val Asp Gln Leu Val Lys Cys Ser His Glu Arg Ser Ile
        260                 265                 270
His Leu Phe Ile Asp Ser Leu Leu Asn Glu Glu Asn Pro Ser Lys Ala
    275                 280                 285
Tyr Arg Cys Ser Ser Lys Glu Ala Phe Glu Lys Gly Leu Cys Leu Ser
290                 295                 300
Cys Arg Lys Asn Arg Cys Asn Asn Leu Gly Tyr Glu Ile Ser Lys Val
305                 310                 315                 320
Arg Ala Lys Arg Ser Ser Lys Met Tyr Leu Lys Thr Arg Ser Gln Met
            325                 330                 335
Pro Tyr Lys Val Phe His Tyr Gln Val Lys Ile His Phe Ser Gly Thr
        340                 345                 350
Glu Ser Glu Thr His Thr Asn Gln Ala Phe Glu Ile Ser Leu Tyr Gly
    355                 360                 365
Thr Val Ala Glu Ser Glu Asn Ile Pro Phe Thr Leu Pro Glu Val Ser
    370                 375                 380
Thr Asn Lys Thr Tyr Ser Phe Leu Ile Tyr Thr Glu Val Asp Ile Gly
385                 390                 395                 400
Glu Leu Leu Met Leu Lys Leu Lys Trp Lys Ser Asp Ser Tyr Phe Ser
            405                 410                 415
Trp Ser Asp Trp Trp Ser Ser Pro Gly Phe Ala Ile Gln Lys Ile Arg
        420                 425                 430
Val Lys Ala Gly Glu Thr Gln Lys Lys Val Ile Phe Cys Ser Arg Glu
    435                 440                 445
Lys Val Ser His Leu Gln Lys Gly Lys Ala Pro Ala Val Phe Val Lys
    450                 455                 460
Cys His Asp Lys Ser Leu Asn Lys Lys Ser Gly
465                 470                 475

<210> SEQ ID NO 13
<211> LENGTH: 3617
<212> TYPE: DNA
<213> ORGANISM: Rattus norvegicus
<220> FEATURE:
<221> NAME/KEY: CDS
<222> LOCATION: (175)..(1599)

<400> SEQUENCE: 13
ttctgcccct tgtagctgtt ctgccctccc ctttaaaggt tgacttgccc cgcggcgctc      60
caccgcgctc tagtcctctg acgcctccgg ctcaacccct tgcaacgcgg atccccgccc     120
```

```
                                                          -continued gcctgactgc ccgcgcagcg cagttccagc agcaaagcag aagggcgcgc cgag atg             177
                                                               Met
                                                               1 gag agc aaa gcc ctg ctc ctg gtg gcc ctg gga gtt tgg ctc cag agt             225
Glu Ser Lys Ala Leu Leu Leu Val Ala Leu Gly Val Trp Leu Gln Ser
        5              10                  15 ttg acc gcc ttc cgc gga ggg gtg gcc gca gca gac ggg gga aga gat             273
Leu Thr Ala Phe Arg Gly Gly Val Ala Ala Ala Asp Gly Gly Arg Asp
     20              25                  30 ttc tca gac atc gaa agt aaa ttt gcc cta agg acc cct gaa gac aca             321
Phe Ser Asp Ile Glu Ser Lys Phe Ala Leu Arg Thr Pro Glu Asp Thr
 35              40                  45 gct gag gac act tgt cat ctg att cct gga tta gca gac tct gtg tct             369
Ala Glu Asp Thr Cys His Leu Ile Pro Gly Leu Ala Asp Ser Val Ser
 50              55                  60                  65 aac tgc cac ttc aac cac agc agc aaa acc ttt gtg gtg atc cat gga             417
Asn Cys His Phe Asn His Ser Ser Lys Thr Phe Val Val Ile His Gly
             70                  75                  80 tgg acg gtg aca gga atg tat gag agt tgg gtg ccc aaa ctt gtg gct             465
Trp Thr Val Thr Gly Met Tyr Glu Ser Trp Val Pro Lys Leu Val Ala
             85                  90                  95 gcc cta tac aaa aga gaa cct gac tcc aat gtc att gta gta gac tgg             513
Ala Leu Tyr Lys Arg Glu Pro Asp Ser Asn Val Ile Val Val Asp Trp
            100                 105                 110 ttg tat cgg gcc cag caa cat tat cca gtg tct gcc ggc tat acc aag             561
Leu Tyr Arg Ala Gln Gln His Tyr Pro Val Ser Ala Gly Tyr Thr Lys
        115                 120                 125 ctg gtg gga aat gat gtg gcc agg ttc atc aac tgg ctg gag gaa gaa             609
Leu Val Gly Asn Asp Val Ala Arg Phe Ile Asn Trp Leu Glu Glu Glu
130                 135                 140                 145 ttt aac tac ccc cta gac aat gtc cac ctc tta ggg tac agt ctt gga             657
Phe Asn Tyr Pro Leu Asp Asn Val His Leu Leu Gly Tyr Ser Leu Gly
            150                 155                 160 gcc cat gct gct ggc gtg gca gga agt ctg acc aac aag aag gtc aat             705
Ala His Ala Ala Gly Val Ala Gly Ser Leu Thr Asn Lys Lys Val Asn
        165                 170                 175 aga att act ggc ttg gat cca gct ggg cct aac ttt gag tat gca gaa             753
Arg Ile Thr Gly Leu Asp Pro Ala Gly Pro Asn Phe Glu Tyr Ala Glu
        180                 185                 190 gcc cct agt cgc ctt tct cct gat gat gcg gat ttc gta gat gtc tta             801
Ala Pro Ser Arg Leu Ser Pro Asp Asp Ala Asp Phe Val Asp Val Leu
    195                 200                 205 cac aca ttt acc agg ggg tcg cct ggt cga agt att ggg atc cag aaa             849
His Thr Phe Thr Arg Gly Ser Pro Gly Arg Ser Ile Gly Ile Gln Lys
210                 215                 220                 225 cca gta ggg cat gtt gat att tat ccc aat gga ggc act ttc cag cca             897
Pro Val Gly His Val Asp Ile Tyr Pro Asn Gly Gly Thr Phe Gln Pro
            230                 235                 240 gga tgc aac att gga gaa gcc att cgt gta att gca gag aag ggg ctt             945
Gly Cys Asn Ile Gly Glu Ala Ile Arg Val Ile Ala Glu Lys Gly Leu
        245                 250                 255 gga gat gtg gac cag ctg gtg aag tgc tcg cac gag cgc tcc atc cat             993
Gly Asp Val Asp Gln Leu Val Lys Cys Ser His Glu Arg Ser Ile His
        260                 265                 270 ctc ttc att gac tcc ctg ctg aat gaa gaa aac ccc agc aag gca tac            1041
Leu Phe Ile Asp Ser Leu Leu Asn Glu Glu Asn Pro Ser Lys Ala Tyr
    275                 280                 285 agg tgc aat tcc aag gag gcc ttt gag aaa ggg ctc tgc ctg agt tgc            1089
Arg Cys Asn Ser Lys Glu Ala Phe Glu Lys Gly Leu Cys Leu Ser Cys
290                 295                 300                 305
```

```
aga aag aat cgc tgt aac aac gtg ggc tat gag atc aac aag gtc aga    1137
Arg Lys Asn Arg Cys Asn Asn Val Gly Tyr Glu Ile Asn Lys Val Arg
                310                 315                 320 gcc aag aga agc agt aag atg tac ctg aag act cgc tct cag atg ccc    1185
Ala Lys Arg Ser Ser Lys Met Tyr Leu Lys Thr Arg Ser Gln Met Pro
            325                 330                 335 tac aaa gta ttc cat tac caa gtc aag att cac ttt tct gga act gag    1233
Tyr Lys Val Phe His Tyr Gln Val Lys Ile His Phe Ser Gly Thr Glu
        340                 345                 350 aat gac aag caa aac aac cag gcc ttc gag att tct ctg tat ggc aca    1281
Asn Asp Lys Gln Asn Asn Gln Ala Phe Glu Ile Ser Leu Tyr Gly Thr
    355                 360                 365 gtg gct gaa agt gag aac att ccc ttc acc ctg ccg gag gtc gcc aca    1329
Val Ala Glu Ser Glu Asn Ile Pro Phe Thr Leu Pro Glu Val Ala Thr
370                 375                 380                 385 aat aaa acc tac tcc ttc ttg att tac acg gag gtg gac atc ggg gaa    1377
Asn Lys Thr Tyr Ser Phe Leu Ile Tyr Thr Glu Val Asp Ile Gly Glu
                390                 395                 400 ttg ctg atg atg aag ctt aag tgg aag aac gac tcc tac ttc cgc tgg    1425
Leu Leu Met Met Lys Leu Lys Trp Lys Asn Asp Ser Tyr Phe Arg Trp
            405                 410                 415 tca gac tgg tgg agc agt ccc agc ttt gtc atc gag aag atc cga gtg    1473
Ser Asp Trp Trp Ser Ser Pro Ser Phe Val Ile Glu Lys Ile Arg Val
        420                 425                 430 aaa gcc gga gag act cag aaa aag gtc atc ttc tgt gcc agg gag aaa    1521
Lys Ala Gly Glu Thr Gln Lys Lys Val Ile Phe Cys Ala Arg Glu Lys
    435                 440                 445 gtt tct cat ctg cag aaa gga aag gac gct gca gtg ttt gtg aaa tgc    1569
Val Ser His Leu Gln Lys Gly Lys Asp Ala Ala Val Phe Val Lys Cys
450                 455                 460                 465 cat gac aag tct ctg aag aag tcg ggc tga cactggacaa accaacaaga      1619
His Asp Lys Ser Leu Lys Lys Ser Gly
                470 gaagaaagca tctgagttct tgaagaccg aagaaatga agtaaatttt atttaaaaaa    1679 ataccccttg tttgggtgtt tgaaagtgga ttttcctgag tattaatccc agctatatct   1739 tgttagttaa atagaagaca gtgtcaaata ttaaaaggtg gctaacacaa cgtgaggaac   1799 ctaatggccg atagcatgtc ctccagcatc agaagacagc agagaggaga agcatgccat   1859 cttatatccc ttaagaagga atcatttgtt cccaaccata caagactcct tcatgtgacc   1919 catttggtca tggtctaaaa ttagtaaggg cctcttattt tcattagatc tctgaggttt   1979 taaattgaga ccttctcaaa gttctcttga agtctaatat agacaacatt tttttgtgct   2039 gtgagtcaga tccatttctt tagcagttga acagctggc cattgtaact agttcttta   2099 ccatcaggat atagcacccc taccaaataa aataaataaa taaagtgacc agggacatgt   2159 gactttgcaa aagcaatgga cgacgtggct cgtggattcc tgacccttag tcccaccaca   2219 acgaagtaca agtcagtaga ggtacaaaac ctagactgag taattcttag tagacttcaa   2279 gttttatggc ttaattcctc tgtctttaa aaacgtgtca catattataa cattattctc    2339 tagacagatg ttgaaatgag cttgtgattc aggtgacata tgaattgagc tgagagaaaa   2399 taatgccctg gctgatttta tttctctgtt ttgctttctt gagaaaagga atacttgtcc   2459 cactccgtat ctgagcctga ccaagaacta aactatgtac ttcaggctta ccttgaactc   2519 tcaaccatcc tgccttggct tcctgagtgc tgggagcttg ataaccataa ttttattatc   2579 agatttttct tagtcatttt caccaataga acacattcaa tgcccaatcg ttagcatttc   2639
```

-continued

```
gtttgagact catcttgacc gtacctctgt cacacgtcta acacatcaca ttaatttcta    2699
gtttagaagt gatcaagttc aaattctgca ctgcgcaaag tacaagtttt agagcaggac    2759 cattttttt ttaccacgta aaagtcgaaa ttactaggaa atgtgtatat cgatgcttgt     2819
acactgttgc gtgcaaagtg aggagccttc tattgtgata gccatagaca gtaccaggct    2879
cgttgccgct cttttgtttt actataaaaa aataatgaag aattatttat gaacaagatc    2939
tcatatgttc agattgcttt tactattcat caatataaaa tgttaaaaaa aaaaaataaa    2999
acaagttcta tctcagaggc tgttgctggg aacagaaact gtgaaatgtg tgggtatctg    3059
aacacctaca cacaagcaaa gccccacaag agtctttgtc attcaatgtc attcagaaag    3119
gaaagagtca agagatatac cataatatgt cagagaagta gttccagata tgctggaatg    3179
ctagcccttg ctaggagaaa gttggttgtg cctatgtaat ataggacaaa agtgactggt    3239
ttcattaggc tcagtgtcat tctaacaata aaatgatgta ccatatgtca ccagcatccc    3299
cattattgct aattcatggc agtatatacg tacatatctc aatgatgctt tgactttaaa    3359
ttttatttat tagctgtaaa taatgtgtgg gtgtgtaagg aagcttgtaa acactggaaa    3419
cgctgttgtg gctatctggg gtgtagattt gtggtgctaa ctctgtgtcc acctccatca    3479
gtgattgtct cactgagcca actcactctg atgaacagca caatggaata gcttttgaag    3539
gaagaaaata aactcacctg tgtgaagaaa tgggatctgc tttcaataaa atcgagaacg    3599
ttttatccgg aatccgcg                                                  3617
```

<210> SEQ ID NO 14
<211> LENGTH: 474
<212> TYPE: PRT
<213> ORGANISM: Rattus norvegicus

<400> SEQUENCE: 14

```
Met Glu Ser Lys Ala Leu Leu Leu Val Ala Leu Gly Val Trp Leu Gln
1               5                   10                  15

Ser Leu Thr Ala Phe Arg Gly Gly Val Ala Ala Ala Asp Gly Gly Arg
            20                  25                  30

Asp Phe Ser Asp Ile Glu Ser Lys Phe Ala Leu Arg Thr Pro Glu Asp
        35                  40                  45

Thr Ala Glu Asp Thr Cys His Leu Ile Pro Gly Leu Ala Asp Ser Val
    50                  55                  60

Ser Asn Cys His Phe Asn His Ser Ser Lys Thr Phe Val Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Tyr Arg Ala Gln Gln His Tyr Pro Val Ser Ala Gly Tyr Thr
        115                 120                 125

Lys Leu Val Gly Asn Asp Val Ala Arg Phe Ile Asn Trp Leu Glu Glu
    130                 135                 140

Glu Phe Asn Tyr Pro Leu Asp Asn Val His Leu Leu Gly Tyr Ser Leu
145                 150                 155                 160

Gly Ala His Ala Ala Gly Val Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
```

-continued

```
                195                 200                 205
Leu His Thr Phe Thr Arg Gly Ser Pro Gly Arg Ser Ile Gly Ile Gln
    210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Lys Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Asn Ser Lys Glu Ala Phe Glu Lys Gly Leu Cys Leu Ser
    290                 295                 300

Cys Arg Lys Asn Arg Cys Asn Asn Val Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Asn Asp Lys Gln Asn Asn Gln Ala Phe Glu Ile Ser Leu Tyr Gly
        355                 360                 365

Thr Val Ala Glu Ser Glu Asn Ile Pro Phe Thr Leu Pro Glu Val Ala
    370                 375                 380

Thr Asn Lys Thr Tyr Ser Phe Leu Ile Tyr Thr Glu Val Asp Ile Gly
385                 390                 395                 400

Glu Leu Leu Met Met Lys Leu Lys Trp Lys Asn Asp Ser Tyr Phe Arg
                405                 410                 415

Trp Ser Asp Trp Trp Ser Ser Pro Ser Phe Val Ile Glu Lys Ile Arg
            420                 425                 430

Val Lys Ala Gly Glu Thr Gln Lys Val Ile Phe Cys Ala Arg Glu
        435                 440                 445

Lys Val Ser His Leu Gln Lys Gly Lys Asp Ala Ala Val Phe Val Lys
450                 455                 460

Cys His Asp Lys Ser Leu Lys Lys Ser Gly
465                 470

<210> SEQ ID NO 15
<211> LENGTH: 3969
<212> TYPE: DNA
<213> ORGANISM: Mus musculus
<220> FEATURE:
<221> NAME/KEY: CDS
<222> LOCATION: (200)..(1624)

<400> SEQUENCE: 15
tgtcagactc tcgatttctc ctcctactcc tcctccgagg aattctgcgc cctgtaactg      60
ttctgccctc ccctttaaag gttgacttgc ctacggcgc tccaccgcgc tccagtcctc     120
ttgcgcctcc tgctcaaccc gctcctgact gccccacgcc gcgtagttcc agcagcaaag     180
cagaagggtg caccgggag atg gag agc aaa gcc ctg ctc ctg gtg gtc ctg      232
                     Met Glu Ser Lys Ala Leu Leu Leu Val Val Leu
                       1               5                  10 gga gtt tgg ctc cag agt ttg acc gcc ttc cga gga ggg gtg gcc gca      280
Gly Val Trp Leu Gln Ser Leu Thr Ala Phe Arg Gly Gly Val Ala Ala
            15                  20                  25 gca gac gca gga aga gat ttc tca gac atc gaa agc aaa ttt gcc cta      328
```

```
                    Ala Asp Ala Gly Arg Asp Phe Ser Asp Ile Glu Ser Lys Phe Ala Leu
                            30                  35                  40 agg acc cct gaa gac aca gct gag gac act tgt cat ctc att cct gga          376
Arg Thr Pro Glu Asp Thr Ala Glu Asp Thr Cys His Leu Ile Pro Gly
 45                  50                  55 tta gca gac tct gtg tct aac tgc cac ttc aac cac agc agc aag acc          424
Leu Ala Asp Ser Val Ser Asn Cys His Phe Asn His Ser Ser Lys Thr
 60                  65                  70                  75 ttc gtg gtg atc cat gga tgg acg gta acg gga atg tat gag agt tgg          472
Phe Val Val Ile His Gly Trp Thr Val Thr Gly Met Tyr Glu Ser Trp
                     80                  85                  90 gtg ccc aaa ctt gtg gcc gcc ctg tac aag aga gaa cct gac tcc aat          520
Val Pro Lys Leu Val Ala Ala Leu Tyr Lys Arg Glu Pro Asp Ser Asn
         95                 100                 105 gtc att gta gta gac tgg ttg tat cgg gcc cag caa cat tat cca gtg          568
Val Ile Val Val Asp Trp Leu Tyr Arg Ala Gln Gln His Tyr Pro Val
            110                 115                 120 tca gct ggc tac acc aag ctg gtg gga aat gat gtg gcc aga ttc atc          616
Ser Ala Gly Tyr Thr Lys Leu Val Gly Asn Asp Val Ala Arg Phe Ile
125                 130                 135 aac tgg atg gag gag gag ttt aag tac ccc cta gac aac gtc cac ctc          664
Asn Trp Met Glu Glu Glu Phe Lys Tyr Pro Leu Asp Asn Val His Leu
140                 145                 150                 155 tta ggg tac agc ctt gga gcc cat gct gct ggc gta gca gga agt ctg          712
Leu Gly Tyr Ser Leu Gly Ala His Ala Ala Gly Val Ala Gly Ser Leu
                    160                 165                 170 acc aat aag aag gtc aat aga att act ggt ttg gat cca gct ggg cct          760
Thr Asn Lys Lys Val Asn Arg Ile Thr Gly Leu Asp Pro Ala Gly Pro
                175                 180                 185 aac ttt gag tat gca gaa gcc ccc agt cgc ctt tct cct gat gac gct          808
Asn Phe Glu Tyr Ala Glu Ala Pro Ser Arg Leu Ser Pro Asp Asp Ala
        190                 195                 200 gat ttt gta gat gtc tta cac aca ttt acc agg ggg tca cct ggt cga          856
Asp Phe Val Asp Val Leu His Thr Phe Thr Arg Gly Ser Pro Gly Arg
205                 210                 215 agt att ggg atc cag aaa cca gtg ggg cat gtt gac att tat ccc aat          904
Ser Ile Gly Ile Gln Lys Pro Val Gly His Val Asp Ile Tyr Pro Asn
220                 225                 230                 235 gga ggc act ttc cag cca gga tgc aac att gga gaa gcc atc cgt gtg          952
Gly Gly Thr Phe Gln Pro Gly Cys Asn Ile Gly Glu Ala Ile Arg Val
                    240                 245                 250 att gca gag aga gga ctc gga gac gtg gac cag ctg gtg aag tgc tcg         1000
Ile Ala Glu Arg Gly Leu Gly Asp Val Asp Gln Leu Val Lys Cys Ser
                255                 260                 265 cat gag cgc tcc att cat ctc ttc att gac tcc ctg ctg aat gaa gaa         1048
His Glu Arg Ser Ile His Leu Phe Ile Asp Ser Leu Leu Asn Glu Glu
        270                 275                 280 aac ccc agc aaa gca tac agg tgc aac tcc aag gaa gcc ttt gag aaa         1096
Asn Pro Ser Lys Ala Tyr Arg Cys Asn Ser Lys Glu Ala Phe Glu Lys
285                 290                 295 ggg ctc tgc ctg agt tgt aga aag aat cgc tgt aac aat ctg ggc tat         1144
Gly Leu Cys Leu Ser Cys Arg Lys Asn Arg Cys Asn Asn Leu Gly Tyr
300                 305                 310                 315 gag atc aac aag gtc aga gcc aag aga agc agc aag atg tac ctg aag         1192
Glu Ile Asn Lys Val Arg Ala Lys Arg Ser Ser Lys Met Tyr Leu Lys
                    320                 325                 330 act cgc tct cag atg ccc tac aaa gtg ttc cat tac caa gtc aag att         1240
Thr Arg Ser Gln Met Pro Tyr Lys Val Phe His Tyr Gln Val Lys Ile
                335                 340                 345
```

```
cac ttt tct ggg act gag aat ggc aag caa cac aac cag gcc ttc gaa     1288
His Phe Ser Gly Thr Glu Asn Gly Lys Gln His Asn Gln Ala Phe Glu
            350                 355                 360 att tct ctg tac ggc aca gtg gcc gag agc gag aac att ccc ttc acc     1336
Ile Ser Leu Tyr Gly Thr Val Ala Glu Ser Glu Asn Ile Pro Phe Thr
365                 370                 375 ctg ccc gag gtt tcc aca aat aaa acc tac tcc ttc ttg att tac acg     1384
Leu Pro Glu Val Ser Thr Asn Lys Thr Tyr Ser Phe Leu Ile Tyr Thr
380                 385                 390                 395 gag gtg gac atc gga gaa ctg ctc atg atg aag ctt aag tgg atg agc     1432
Glu Val Asp Ile Gly Glu Leu Leu Met Met Lys Leu Lys Trp Met Ser
                400                 405                 410 gac tcc tac ttc agc tgg ccc gac tgg tgg agc agc ccc agc ttc gtc     1480
Asp Ser Tyr Phe Ser Trp Pro Asp Trp Trp Ser Ser Pro Ser Phe Val
            415                 420                 425 atc gag agg atc cga gtg aaa gcc gga gag act cag aaa aag gtc atc     1528
Ile Glu Arg Ile Arg Val Lys Ala Gly Glu Thr Gln Lys Lys Val Ile
        430                 435                 440 ttc tgt gct agg gag aaa gtt tct cat ctg cag aag gga aag gac tca     1576
Phe Cys Ala Arg Glu Lys Val Ser His Leu Gln Lys Gly Lys Asp Ser
    445                 450                 455 gca gtg ttt gtg aaa tgc cat gac aag tct ctg aag aag tct ggc tga     1624
Ala Val Phe Val Lys Cys His Asp Lys Ser Leu Lys Lys Ser Gly
460                 465                 470 cactggacaa acaaacaaga gaagaaagca tccgagttct tgaagacag aagaaaacaa    1684
agtaaattta atttaaaaaa ataatacccct tgtttgggtg tttgaaagtg ggttttcctg  1744
agtattaatc ccagctctat cttgttagtt aaacagaaga cagtctcaaa tattaaacgg   1804
tggctaaccc agggtgagga atctaatggc ccatagcagg tcttccagca tcagaagaca   1864
tcaggcagga gaaacatgct gtcttgtatc ccttaagaag gaatcatttg ttcccaacaa   1924
tataagactc catcatgtga cccatttggt catggtctaa aattagtaag aactctgagg   1984
ttttatattg agaccttttc aaagttttct caaagtctaa tatagacaat atttttgtg    2044
gcatgagtca ggtccatttc tttagcggtt gaaacacctg gcctttgcaa ctagtttttt   2104
tttaccattg ggatatattc cccccaccaa aaaaaaaaa aaaaaaagt aaccaggaac     2164
gtgtgacttg gcaaaagcag ttgaagacat ggctcatgaa gtcctgaccc ttggtcccac   2224
cacaacaaag tacaagtcaa cagagataca aaacctagac tgagtaattc ttaatagact   2284
tgaattttta tggcttaatc cttctatctt ttaaatattt gtcagatatt ttaacattgt   2344
tctctggata gatgttgaaa atgagcttat aagctgggca atggtggcgc tcaccttaa    2404
tcccagcact tggcaggcag aggcaggcgg atttctgagt tcaaggccag cctggtttac   2464
agagtgagtt ccaggacatc cagagctaca cagagaaacc ctgtctcggg aaaaaaaaa    2524
aaaagaaga gaaggagaa gaagagggag ggagggaggg agggagggag ggagggagga    2584
aggaaggaag gaaggaagga aggaaggaag gaaggaagga aggaaggaag aaagaaagaa   2644
agaaagaaag aaagaaagaa agaagaaag aaagaaagaa agaaagaaag aaagaaatg    2704
agcttgtaat tgaggtgaca cataaatttt gctgaaagac aaaaatgcct aggttgattt   2764
tacttctctt ttttgctttc ttgaaaaaag tcacaattgt cccatgctgt aaccaagtct   2824
ggcctagaac taaactatgt atttcaggct ggccttgaac tctcaaccat cctgccttag   2884
cttcctgtgt cctgggagct tgagaaccgt aatttatta tcagatttt cttacttgtt    2944
ttcatcaatt tgaaatgccc aatatccaat actttgtatt tcatttgaga ctcatctccg   3004
ccatgcctct gtcacacttc taacacatca cattaatttc tagtttagat gtgatcaagt   3064
```

```
tcaaattctg cactgtgcaa agtacaagtt ttagagcagg accattttttt ttatcacata    3124 aaagttgaaa ttactagaaa atgtgcatat ggatgcttgt aaactgctgt gcaaagagaa    3184
gagccctcaa ctgtaatagc tatagaaagt accaggattg ttgccgctgt tttgttttac    3244
cttaacaaca acaacaacaa aaatcaataa tgaagaatta tttatgaacg agatctcaca    3304
ttttcagatt gcttttatta ttcattaatg taaaatgata agaagatct atctcagagg     3364 ctatagctgg gagcagaaac tgtgaaattt gtgggtatct gaacaccaac ccacatgcaa    3424
aaccccacaa gtgtagtcgt cattcaatgt gattcagaaa ggaaagagtc aagggatata    3484
ctggaatatg ttagagaagt agttccagat atgctggaat gttagccctt gctaggagaa    3544
agctggttgt gcctatgtaa ataggacaaa aggtgaccga tttcatcaag tttggagtca    3604
attctaacaa taaaaatatg tataatttgt taccggcatc cccattattg ctaattcatt    3664
acagtatata cacatccatg catacatatg tcaatgatgc tttagctttc aatttattta    3724
ttagctgtaa ataatgtgtg ggtatgtaag aatgcttgta aacactggaa agtctgttgt    3784
ggttatctgc agtatagatt tgtggtgcta actttgtgtc cgtctccatc catgattgtc    3844
tgtctcactg agccaactta actctgatga aacagtacaa tgaaataggc ttttgaaaga    3904
agaaaactca cctgtgtgaa gaatggtat ctgctttcaa taaaactgag aacattttat    3964
catga                                                                3969

<210> SEQ ID NO 16
<211> LENGTH: 474
<212> TYPE: PRT
<213> ORGANISM: Mus musculus

<400> SEQUENCE: 16

Met Glu Ser Lys Ala Leu Leu Val Val Leu Gly Val Trp Leu Gln
1               5                   10                  15

Ser Leu Thr Ala Phe Arg Gly Gly Val Ala Ala Asp Ala Gly Arg
                20                  25                  30

Asp Phe Ser Asp Ile Glu Ser Lys Phe Ala Leu Arg Thr Pro Glu Asp
            35                  40                  45

Thr Ala Glu Asp Thr Cys His Leu Ile Pro Gly Leu Ala Asp Ser Val
    50                  55                  60

Ser Asn Cys His Phe Asn His Ser Ser Lys Thr Phe Val Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Tyr Arg Ala Gln Gln His Tyr Pro Val Ser Ala Gly Tyr Thr
        115                 120                 125

Lys Leu Val Gly Asn Asp Val Ala Arg Phe Ile Asn Trp Met Glu Glu
    130                 135                 140

Glu Phe Lys Tyr Pro Leu Asp Asn Val His Leu Leu Gly Tyr Ser Leu
145                 150                 155                 160

Gly Ala His Ala Ala Gly Val Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
        195                 200                 205
```

```
Leu His Thr Phe Thr Arg Gly Ser Pro Gly Arg Ser Ile Gly Ile Gln
        210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Asn Ser Lys Glu Ala Phe Glu Lys Gly Leu Cys Leu Ser
    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Asn Gly Lys Gln His Asn Gln Ala Phe Glu Ile Ser Leu Tyr Gly
        355                 360                 365

Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
385                 390                 395                 400

Glu Leu Leu Met Met Lys Leu Lys Trp Met Ser Asp Ser Tyr Phe Ser
                405                 410                 415

Trp Pro Asp Trp Trp Ser Ser Pro Ser Phe Val Ile Glu Arg Ile Arg
            420                 425                 430

Val Lys Ala Gly Glu Thr Gln Lys Lys Val Ile Phe Cys Ala Arg Glu
        435                 440                 445

Lys Val Ser His Leu Gln Lys Gly Lys Asp Ser Ala Val Phe Val Lys
    450                 455                 460

Cys His Asp Lys Ser Leu Lys Lys Ser Gly
465                 470

<210> SEQ ID NO 17
<211> LENGTH: 2328
<212> TYPE: DNA
<213> ORGANISM: Gallus gallus
<220> FEATURE:
<221> NAME/KEY: CDS
<222> LOCATION: (115)..(1587)

<400> SEQUENCE: 17
ccttcacagt cgtgtgtttt agaacttagt tattctattt tgttttgttt gcttttaacc      60
ttaaccatcc ccccccctc ctcccactga aacttttcg ccgctgcaca acgc atg         117
                                                          Met
                                                          1 gag cga gga cgc ggg atg ggg aag aca gcg ctg ctg gct gtg ctg tgc       165
Glu Arg Gly Arg Gly Met Gly Lys Thr Ala Leu Leu Ala Val Leu Cys
        5                   10                  15 ctc tgc ctg cgc ggg gcc gcc ggc tcc gat ccc gaa gct gag atg aat       213
Leu Cys Leu Arg Gly Ala Ala Gly Ser Asp Pro Glu Ala Glu Met Asn
        20                  25                  30 ttt gag gga atc gag agc aag ttt tcc tta aga aca cct gca gag cct       261
Phe Glu Gly Ile Glu Ser Lys Phe Ser Leu Arg Thr Pro Ala Glu Pro
```

-continued

|  |  |  |  |  |  |  |  |  |  |  |  |  |  |  |  |
|---|---|---|---|---|---|---|---|---|---|---|---|---|---|---|---|
|  | 35 |  |  |  | 40 |  |  |  |  | 45 |  |  |  |  |  |
| gat | gaa | gat | gtc | tgc | tac | ctg | gtt | cct | gga | cag | atg | gac | agc | ttg | gca | 309 |
| Asp | Glu | Asp | Val | Cys | Tyr | Leu | Val | Pro | Gly | Gln | Met | Asp | Ser | Leu | Ala |  |
| 50 |  |  |  | 55 |  |  |  |  | 60 |  |  |  |  | 65 |  |  |
| cag | tgc | aac | ttc | aac | cat | acc | agt | aaa | acc | ttt | gtg | gtg | atc | cat | ggg | 357 |
| Gln | Cys | Asn | Phe | Asn | His | Thr | Ser | Lys | Thr | Phe | Val | Val | Ile | His | Gly |  |
|  |  |  | 70 |  |  |  |  | 75 |  |  |  |  | 80 |  |  |  |
| tgg | acg | gtg | aca | gga | atg | tat | gaa | agc | tgg | gtc | cca | aag | cta | gtg | gat | 405 |
| Trp | Thr | Val | Thr | Gly | Met | Tyr | Glu | Ser | Trp | Val | Pro | Lys | Leu | Val | Asp |  |
|  |  | 85 |  |  |  |  | 90 |  |  |  |  | 95 |  |  |  |  |
| gct | ctg | tac | aag | agg | gaa | cct | gat | tca | aat | gtc | att | gtt | gtg | gac | tgg | 453 |
| Ala | Leu | Tyr | Lys | Arg | Glu | Pro | Asp | Ser | Asn | Val | Ile | Val | Val | Asp | Trp |  |
| 100 |  |  |  |  | 105 |  |  |  |  | 110 |  |  |  |  |  |  |
| ctg | gtt | cga | gct | cag | cag | cac | tac | cca | gtg | tct | gct | gct | tac | acg | aag | 501 |
| Leu | Val | Arg | Ala | Gln | Gln | His | Tyr | Pro | Val | Ser | Ala | Ala | Tyr | Thr | Lys |  |
|  | 115 |  |  |  |  | 120 |  |  |  |  | 125 |  |  |  |  |  |
| ctg | gtg | gga | aag | gat | gtt | gcc | atg | ttc | att | gat | tgg | atg | gag | gag | aaa | 549 |
| Leu | Val | Gly | Lys | Asp | Val | Ala | Met | Phe | Ile | Asp | Trp | Met | Glu | Glu | Lys |  |
| 130 |  |  |  |  | 135 |  |  |  |  | 140 |  |  |  |  | 145 |  |
| ttc | aat | tac | cct | ctc | aac | aat | gtc | cac | ttg | ctg | ggg | tac | agt | ctg | ggt | 597 |
| Phe | Asn | Tyr | Pro | Leu | Asn | Asn | Val | His | Leu | Leu | Gly | Tyr | Ser | Leu | Gly |  |
|  |  |  |  | 150 |  |  |  |  | 155 |  |  |  |  | 160 |  |  |
| gct | cat | gct | gct | ggg | att | gct | gga | agt | tta | acc | aag | aaa | aag | gtg | aac | 645 |
| Ala | His | Ala | Ala | Gly | Ile | Ala | Gly | Ser | Leu | Thr | Lys | Lys | Lys | Val | Asn |  |
|  |  | 165 |  |  |  |  | 170 |  |  |  |  | 175 |  |  |  |  |
| aga | att | act | ggt | ctg | gat | cct | gct | ggt | ccc | acc | ttt | gag | tat | gct | gat | 693 |
| Arg | Ile | Thr | Gly | Leu | Asp | Pro | Ala | Gly | Pro | Thr | Phe | Glu | Tyr | Ala | Asp |  |
|  |  | 180 |  |  |  |  | 185 |  |  |  |  | 190 |  |  |  |  |
| gcc | cct | atc | cgc | ctc | tcc | ccg | gat | gat | gct | gac | ttt | gtg | gat | gtc | ctg | 741 |
| Ala | Pro | Ile | Arg | Leu | Ser | Pro | Asp | Asp | Ala | Asp | Phe | Val | Asp | Val | Leu |  |
| 195 |  |  |  |  | 200 |  |  |  |  | 205 |  |  |  |  |  |  |
| cac | acc | tac | act | cga | ggc | tct | cca | gat | cgc | agc | att | ggg | att | cag | aag | 789 |
| His | Thr | Tyr | Thr | Arg | Gly | Ser | Pro | Asp | Arg | Ser | Ile | Gly | Ile | Gln | Lys |  |
| 210 |  |  |  |  | 215 |  |  |  |  | 220 |  |  |  |  | 225 |  |
| cct | gtt | gga | cac | att | gat | atc | tac | cct | aat | ggt | gga | ggt | ttc | cag | cca | 837 |
| Pro | Val | Gly | His | Ile | Asp | Ile | Tyr | Pro | Asn | Gly | Gly | Gly | Phe | Gln | Pro |  |
|  |  |  |  | 230 |  |  |  |  | 235 |  |  |  |  | 240 |  |  |
| ggc | tgc | aac | ttg | gga | gaa | gct | ctc | cgc | ctg | att | gct | gaa | aaa | ggc | ttt | 885 |
| Gly | Cys | Asn | Leu | Gly | Glu | Ala | Leu | Arg | Leu | Ile | Ala | Glu | Lys | Gly | Phe |  |
|  |  | 245 |  |  |  |  | 250 |  |  |  |  | 255 |  |  |  |  |
| tca | gat | gtg | gat | cag | ctg | gtg | aag | tgc | tct | cat | gaa | cga | tcc | atc | cat | 933 |
| Ser | Asp | Val | Asp | Gln | Leu | Val | Lys | Cys | Ser | His | Glu | Arg | Ser | Ile | His |  |
|  | 260 |  |  |  |  | 265 |  |  |  |  | 270 |  |  |  |  |  |
| ctc | ttc | att | gac | tca | ctc | ctc | tat | gaa | gag | aag | ccc | agc | atg | gcc | tac | 981 |
| Leu | Phe | Ile | Asp | Ser | Leu | Leu | Tyr | Glu | Glu | Lys | Pro | Ser | Met | Ala | Tyr |  |
| 275 |  |  |  |  | 280 |  |  |  |  | 285 |  |  |  |  |  |  |
| cgc | tgc | aac | aca | aaa | gag | gcc | ttt | gag | aag | ggc | ctc | tgc | cta | agc | tgc | 1029 |
| Arg | Cys | Asn | Thr | Lys | Glu | Ala | Phe | Glu | Lys | Gly | Leu | Cys | Leu | Ser | Cys |  |
| 290 |  |  |  |  | 295 |  |  |  |  | 300 |  |  |  |  | 305 |  |
| cgg | aag | aac | cgt | tgc | aac | aac | ttg | ggt | tat | aaa | gtc | aac | aga | gtg | aga | 1077 |
| Arg | Lys | Asn | Arg | Cys | Asn | Asn | Leu | Gly | Tyr | Lys | Val | Asn | Arg | Val | Arg |  |
|  |  |  | 310 |  |  |  |  | 315 |  |  |  |  | 320 |  |  |  |
| aca | aag | aga | aac | acc | aaa | atg | tac | ttg | aag | acc | cgt | gct | cag | atg | ccc | 1125 |
| Thr | Lys | Arg | Asn | Thr | Lys | Met | Tyr | Leu | Lys | Thr | Arg | Ala | Gln | Met | Pro |  |
|  |  | 325 |  |  |  |  | 330 |  |  |  |  | 335 |  |  |  |  |
| tac | aaa | gtc | ttc | cat | tat | cag | gtc | aag | ata | cat | ttc | ttt | gga | aag | aca | 1173 |
| Tyr | Lys | Val | Phe | His | Tyr | Gln | Val | Lys | Ile | His | Phe | Phe | Gly | Lys | Thr |  |
|  |  |  | 340 |  |  |  |  | 345 |  |  |  |  | 350 |  |  |  |
| aat | gtg | acc | aag | gta | gac | cag | cca | ttc | ctg | atc | tct | ctg | tat | ggc | act | 1221 |

-continued

| | | | | | | | | | | | | | | |
|---|---|---|---|---|---|---|---|---|---|---|---|---|---|---|
|Asn|Val|Thr|Lys|Val|Asp|Gln|Pro|Phe|Leu|Ile|Ser|Leu|Tyr|Gly|Thr|
| |355| | | |360| | | |365| | | | | | | cta gac gag agt gag aac att cct ttc acg ctg cct gaa gtc tct tcc 1269
Leu Asp Glu Ser Glu Asn Ile Pro Phe Thr Leu Pro Glu Val Ser Ser
370             375             380             385 aac aag acc ttc tcc ttc ctg atc tac aca gaa gtg gac att ggt gac 1317
Asn Lys Thr Phe Ser Phe Leu Ile Tyr Thr Glu Val Asp Ile Gly Asp
            390             395             400 ctg ctt atg cta aag ctg cag tgg gag aaa gat act ttc ttc agc tgg 1365
Leu Leu Met Leu Lys Leu Gln Trp Glu Lys Asp Thr Phe Phe Ser Trp
        405             410             415 tca gac tgg tgg act cca ttt gca ttc acc att cag aga gtc aga gtg 1413
Ser Asp Trp Trp Thr Pro Phe Ala Phe Thr Ile Gln Arg Val Arg Val
    420             425             430 aag tca ggc gaa act cag aaa aag gtg gta ttc tgt tct cga gat ggc 1461
Lys Ser Gly Glu Thr Gln Lys Lys Val Val Phe Cys Ser Arg Asp Gly
435             440             445 agc tca cgt ctt ggt aaa gga gaa gag gca gca ata ttt gtg aag tgc 1509
Ser Ser Arg Leu Gly Lys Gly Glu Glu Ala Ala Ile Phe Val Lys Cys
450             455             460             465 ctg gag cag cct gtc agc agg aag agg gga ggt gcc aag aaa gcc tct 1557
Leu Glu Gln Pro Val Ser Arg Lys Arg Gly Gly Ala Lys Lys Ala Ser
            470             475             480 aaa gaa aat tct gca cac gag tct gct taa aaagtggcaa gaatgagaat 1607
Lys Glu Asn Ser Ala His Glu Ser Ala
        485             490 ttccacactg gggaggagga tggagtctgt tcatccctgt gaactggatg ttcagaacca 1667 aatatataga aatacttatc tgctgctggc ttttgtgcct gcctatacct agctatatta 1727 ggaggcttct tgtaaggaag tctcagcgta caaagttact aaccataaag ttacattaca 1787 ttatctgata gttaagaaca agaaaccccc tgcaacaact tccgaaaggc ttgagtgtta 1847 ggaaggaata agtaattttg cttaatcgtg gtgccttgtg acagtttctt gccatcagtt 1907 cctctttagc agttttgtag tatttattga aaagatgcaa agctctgtac ctggtcctct 1967 ttttagtgtt ttttgtttcc aatttttatt tttttaagag atcttctgga actgcacaga 2027 tctttttttg ttgttctcct ggccttgcta actgaatttt caggcagttc attggctaga 2087 gttcgttgtc ttcaagtggt gtgtttggca agtgagtagt tttctcatgg aaaaaaatac 2147 ccttgtgtgt agagctataa cagagatgtc agggcctggt tcaatatggg gatgaatctt 2207 ctaggttgtg gttatgaatg tgctttactg ggtgtagatg ccaatgcttc ttagcaatag 2267 ttataatctg ttaagatatg taatcctatg cagcttatcc cggaataaat agcaatagga 2327 g 2328

<210> SEQ ID NO 18
<211> LENGTH: 490
<212> TYPE: PRT
<213> ORGANISM: Gallus gallus

<400> SEQUENCE: 18

Met Glu Arg Gly Arg Gly Met Gly Lys Thr Ala Leu Leu Ala Val Leu
1               5                   10                  15

Cys Leu Cys Leu Arg Gly Ala Ala Gly Ser Asp Pro Glu Ala Glu Met
            20                  25                  30

Asn Phe Glu Gly Ile Glu Ser Lys Phe Ser Leu Arg Thr Pro Ala Glu
        35                  40                  45

Pro Asp Glu Asp Val Cys Tyr Leu Val Pro Gly Gln Met Asp Ser Leu

-continued

```
             50                  55                  60
Ala Gln Cys Asn Phe Asn His Thr Ser Lys Thr Phe Val Val Ile His
 65                  70                  75                  80

Gly Trp Thr Val Thr Gly Met Tyr Glu Ser Trp Val Pro Lys Leu Val
                 85                  90                  95

Asp Ala Leu Tyr Lys Arg Glu Pro Asp Ser Asn Val Ile Val Val Asp
                100                 105                 110

Trp Leu Val Arg Ala Gln Gln His Tyr Pro Val Ser Ala Ala Tyr Thr
                115                 120                 125

Lys Leu Val Gly Lys Asp Val Ala Met Phe Ile Asp Trp Met Glu Glu
130                 135                 140

Lys Phe Asn Tyr Pro Leu Asn Asn Val His Leu Leu Gly Tyr Ser Leu
145                 150                 155                 160

Gly Ala His Ala Ala Gly Ile Ala Gly Ser Leu Thr Lys Lys Lys Val
                165                 170                 175

Asn Arg Ile Thr Gly Leu Asp Pro Ala Gly Pro Thr Phe Glu Tyr Ala
                180                 185                 190

Asp Ala Pro Ile Arg Leu Ser Pro Asp Asp Ala Asp Phe Val Asp Val
                195                 200                 205

Leu His Thr Tyr Thr Arg Gly Ser Pro Asp Arg Ser Ile Gly Ile Gln
                210                 215                 220

Lys Pro Val Gly His Ile Asp Ile Tyr Pro Asn Gly Gly Phe Gln
225                 230                 235                 240

Pro Gly Cys Asn Leu Gly Glu Ala Leu Arg Leu Ile Ala Glu Lys Gly
                245                 250                 255

Phe Ser Asp Val Asp Gln Leu Val Lys Cys Ser His Glu Arg Ser Ile
                260                 265                 270

His Leu Phe Ile Asp Ser Leu Leu Tyr Glu Glu Lys Pro Ser Met Ala
                275                 280                 285

Tyr Arg Cys Asn Thr Lys Glu Ala Phe Glu Lys Gly Leu Cys Leu Ser
                290                 295                 300

Cys Arg Lys Asn Arg Cys Asn Asn Leu Gly Tyr Lys Val Asn Arg Val
305                 310                 315                 320

Arg Thr Lys Arg Asn Thr Lys Met Tyr Leu Lys Thr Arg Ala Gln Met
                325                 330                 335

Pro Tyr Lys Val Phe His Tyr Gln Val Lys Ile His Phe Phe Gly Lys
                340                 345                 350

Thr Asn Val Thr Lys Val Asp Gln Pro Phe Leu Ile Ser Leu Tyr Gly
                355                 360                 365

Thr Leu Asp Glu Ser Glu Asn Ile Pro Phe Thr Leu Pro Glu Val Ser
370                 375                 380

Ser Asn Lys Thr Phe Ser Phe Leu Ile Tyr Thr Glu Val Asp Ile Gly
385                 390                 395                 400

Asp Leu Leu Met Leu Lys Leu Gln Trp Glu Lys Asp Thr Phe Phe Ser
                405                 410                 415

Trp Ser Asp Trp Trp Thr Pro Phe Ala Phe Thr Ile Gln Arg Val Arg
                420                 425                 430

Val Lys Ser Gly Glu Thr Gln Lys Lys Val Val Phe Cys Ser Arg Asp
                435                 440                 445

Gly Ser Ser Arg Leu Gly Lys Gly Glu Glu Ala Ala Ile Phe Val Lys
                450                 455                 460

Cys Leu Glu Gln Pro Val Ser Arg Lys Arg Gly Gly Ala Lys Lys Ala
465                 470                 475                 480
```

```
                Ser Lys Glu Asn Ser His Glu Ser Ala
                                485                 490

<210> SEQ ID NO 19
<211> LENGTH: 287
<212> TYPE: DNA
<213> ORGANISM: Canis familiaris
<220> FEATURE:
<221> NAME/KEY: CDS
<222> LOCATION: (1)..(285)

<400> SEQUENCE: 19 ctc ttt att gac tct ctg ctg aat gaa gaa aat cca agt aag gcc tac      48
Leu Phe Ile Asp Ser Leu Leu Asn Glu Glu Asn Pro Ser Lys Ala Tyr
1               5                   10                  15 cgg tgc aac tca aag gaa gcc ttt gag aaa ggg ctt tgc ctg agt tgc      96
Arg Cys Asn Ser Lys Glu Ala Phe Glu Lys Gly Leu Cys Leu Ser Cys
            20                  25                  30 aga aag aac cgt tgc aac aac atg ggc tat gag atc aat aag gtc aga     144
Arg Lys Asn Arg Cys Asn Asn Met Gly Tyr Glu Ile Asn Lys Val Arg
        35                  40                  45 gcc aaa aga ggc agc aaa atg tac ctg aag act cgc tct cag atg cct     192
Ala Lys Arg Gly Ser Lys Met Tyr Leu Lys Thr Arg Ser Gln Met Pro
    50                  55                  60 tac aaa gtc ttc cat tac caa gta aag ata cat ttt tct ggg act gag     240
Tyr Lys Val Phe His Tyr Gln Val Lys Ile His Phe Ser Gly Thr Glu
65                  70                  75                  80 agt gat gca cag acc aac cag gcc ttc gag att tct ctg tat ggc ac      287
Ser Asp Ala Gln Thr Asn Gln Ala Phe Glu Ile Ser Leu Tyr Gly
                85                  90                  95

<210> SEQ ID NO 20
<211> LENGTH: 95
<212> TYPE: PRT
<213> ORGANISM: Canis familiaris

<400> SEQUENCE: 20

Leu Phe Ile Asp Ser Leu Leu Asn Glu Glu Asn Pro Ser Lys Ala Tyr
1               5                   10                  15

Arg Cys Asn Ser Lys Glu Ala Phe Glu Lys Gly Leu Cys Leu Ser Cys
            20                  25                  30

Arg Lys Asn Arg Cys Asn Asn Met Gly Tyr Glu Ile Asn Lys Val Arg
        35                  40                  45

Ala Lys Arg Gly Ser Lys Met Tyr Leu Lys Thr Arg Ser Gln Met Pro
    50                  55                  60

Tyr Lys Val Phe His Tyr Gln Val Lys Ile His Phe Ser Gly Thr Glu
65                  70                  75                  80

Ser Asp Ala Gln Thr Asn Gln Ala Phe Glu Ile Ser Leu Tyr Gly
                85                  90                  95

<210> SEQ ID NO 21
<211> LENGTH: 612
<212> TYPE: DNA
<213> ORGANISM: Bos Taurus
<220> FEATURE:
<221> NAME/KEY: CDS
<222> LOCATION: (1)..(207)

<400> SEQUENCE: 21 ctc aaa tgg att agt gat tcc tac ttc agc tgg tcc aac tgg tgg agc      48
Leu Lys Trp Ile Ser Asp Ser Tyr Phe Ser Trp Ser Asn Trp Trp Ser
1               5                   10                  15
```

```
agc ccc ggc ttt gat att ggg aag atc aga gta aag gca gga gag act      96
Ser Pro Gly Phe Asp Ile Gly Lys Ile Arg Val Lys Ala Gly Glu Thr
             20                  25                  30 caa aaa aag gtg atc ttc tgt tcc cgg gag aaa atg tct tat ctg cag     144
Gln Lys Lys Val Ile Phe Cys Ser Arg Glu Lys Met Ser Tyr Leu Gln
             35                  40                  45 aaa gga aag tca cct gtg ata ttt gtg aaa tgc cat gac aag tcc ctg     192
Lys Gly Lys Ser Pro Val Ile Phe Val Lys Cys His Asp Lys Ser Leu
 50                  55                  60 aat aga aag tct ggc tgaaacttgg caaagctacg aagaaagaa cagcatatga      247
Asn Arg Lys Ser Gly
 65 attctatgaa gaatgaagta acttttacaa aagatgccca gtgctttaga tggtgaaatg   307 tggattttcc ggagtattaa ccccagctct agccttatta gttatttag gagacagtct    367 caaatactaa aactaattca atttgaggtg tatagtggcc aaatagcaca tcttccaaca   427 ttaaaaaaat aacagatatg aaaagcactg cattctgtct tttgaaaaaa tatgagttat   487 ttaaaatgat aaaataatca gatctcttca tgtagtaagt ttagccatag cctaaaattg   547 attaaaatct catttttaat tgggattctg cgttttctag actgataacc ttctcagagt   607 tttct                                                               612
```

<210> SEQ ID NO 22
<211> LENGTH: 69
<212> TYPE: PRT
<213> ORGANISM: Bos Taurus

<400> SEQUENCE: 22

```
Leu Lys Trp Ile Ser Asp Ser Tyr Phe Ser Trp Ser Asn Trp Trp Ser
 1               5                  10                  15

Ser Pro Gly Phe Asp Ile Gly Lys Ile Arg Val Lys Ala Gly Glu Thr
             20                  25                  30

Gln Lys Lys Val Ile Phe Cys Ser Arg Glu Lys Met Ser Tyr Leu Gln
             35                  40                  45

Lys Gly Lys Ser Pro Val Ile Phe Val Lys Cys His Asp Lys Ser Leu
 50                  55                  60

Asn Arg Lys Ser Gly
 65
```

<210> SEQ ID NO 23
<211> LENGTH: 1285
<212> TYPE: DNA
<213> ORGANISM: Caenorhabditis elegans
<220> FEATURE:
<221> NAME/KEY: CDS
<222> LOCATION: (342)..(1094)

<400> SEQUENCE: 23

```
atctatgagg aaatgctgag aaacttattt tcaatcactt atcgattcgc ttcatctgat    60
tctccgagga aagtcgtagt ttgtgcaaac ggaacgattg ctgcctggca tccaccacaa   120
cattttccat acgagcatac gaaaccaatt gatctcggtt cactgactaa aaaggatcaa   180
agctctcgtt tgtcagcagc agcaaaagct tcttccattc cacgcgagcc agttaacgct   240
gagctcaagg acatttttcta cacgagcaag cacgagtggg attccagaac tcgcgaagaa   300
cgcctccgca acgtggctgc tccaattcca cgtcgtaaat a atg cgt ctc tcc tca   356
                                              Met Arg Leu Ser Ser
                                               1               5
```

```
cta ctt cgt caa aaa tca aca gta aat gct atc gat ttg ggt cag atc          404
Leu Leu Arg Gln Lys Ser Thr Val Asn Ala Ile Asp Leu Gly Gln Ile
             10                  15                  20 tcg tat ggt gcc gca ttg aaa gaa caa caa aaa tat gta gat ttg gtt          452
Ser Tyr Gly Ala Ala Leu Lys Glu Gln Gln Lys Tyr Val Asp Leu Val
         25                  30                  35 aaa gcg aat aaa tct gaa aca cat tct tta aat ttt ata ttg gct ctc          500
Lys Ala Asn Lys Ser Glu Thr His Ser Leu Asn Phe Ile Leu Ala Leu
     40                  45                  50 gaa cac aca ccg gtt tat aca gtg ggc att cga agt aaa ggt tat aca          548
Glu His Thr Pro Val Tyr Thr Val Gly Ile Arg Ser Lys Gly Tyr Thr
 55                  60                  65 aaa gaa gaa gag aca agg ttg atg aga ctt ggt gca gaa ttt cat aga          596
Lys Glu Glu Glu Thr Arg Leu Met Arg Leu Gly Ala Glu Phe His Arg
70                  75                  80                  85 aca tct cgt gga ggg ctc atc act ttt cat gga cct ggg caa ctt gtt          644
Thr Ser Arg Gly Gly Leu Ile Thr Phe His Gly Pro Gly Gln Leu Val
                 90                  95                 100 cta tat cca att tgc gat gtt cgc aga att tca atc aag caa cta ggt          692
Leu Tyr Pro Ile Cys Asp Val Arg Arg Ile Ser Ile Lys Gln Leu Gly
             105                 110                 115 gtt agg cat ttt gtg gac aag tta gag caa acg att ata gat gca gcg          740
Val Arg His Phe Val Asp Lys Leu Glu Gln Thr Ile Ile Asp Ala Ala
         120                 125                 130 aca gag gga ttt gga atc aaa aat gtt ggc cga act gcg aat aca ggt          788
Thr Glu Gly Phe Gly Ile Lys Asn Val Gly Arg Thr Ala Asn Thr Gly
     135                 140                 145 gta tgg gta tcc aat gaa cgt aaa ctc gct gca att gga att gct gtc          836
Val Trp Val Ser Asn Glu Arg Lys Leu Ala Ala Ile Gly Ile Ala Val
150                 155                 160                 165 tct ggt gga gta tcg tat cac ggg atc gca ata aat tgt aac act gac          884
Ser Gly Gly Val Ser Tyr His Gly Ile Ala Ile Asn Cys Asn Thr Asp
                 170                 175                 180 ctt aga tgg ttc gat aat att gtt gga tgt ggt atc gaa gga gtc tcc          932
Leu Arg Trp Phe Asp Asn Ile Val Gly Cys Gly Ile Glu Gly Val Ser
             185                 190                 195 act act tcc tta tcc cag gaa aca tcc cga aat gtg acc gtt tct gat          980
Thr Thr Ser Leu Ser Gln Glu Thr Ser Arg Asn Val Thr Val Ser Asp
         200                 205                 210 gct cgt cct att ctt ctg aac gct ttt gcc aat aac ttt gaa tgc ctt         1028
Ala Arg Pro Ile Leu Leu Asn Ala Phe Ala Asn Asn Phe Glu Cys Leu
     215                 220                 225 ctc aat gaa ccc aat gat tat tcg aca tgt tcc aat tta aaa att acg         1076
Leu Asn Glu Pro Asn Asp Tyr Ser Thr Cys Ser Asn Leu Lys Ile Thr
230                 235                 240                 245 aat gtt gtt tct agt taa cttcatctcc ttccattagt ttttagtttt              1124
Asn Val Val Ser Ser
                250 tagttctaga tttttcaatt tttattagaa tttatagaa attaccaaat cgccattgtt      1184 ctttgttcat ttaattgttt gtactcccta ctcaattcgc tactcaaatt tggtcgttg      1244 ttgttcccaa tgtcaccct aaaaatgcaa ttttgaaac a                           1285

<210> SEQ ID NO 24
<211> LENGTH: 250
<212> TYPE: PRT
<213> ORGANISM: Caenorhabditis elegans

<400> SEQUENCE: 24

Met Arg Leu Ser Ser Leu Leu Arg Gln Lys Ser Thr Val Asn Ala Ile
```

```
1               5                   10                  15
Asp Leu Gly Gln Ile Ser Tyr Gly Ala Ala Leu Lys Glu Gln Gln Lys
            20                  25                  30

Tyr Val Asp Leu Val Lys Ala Asn Lys Ser Glu Thr His Ser Leu Asn
            35                  40                  45

Phe Ile Leu Ala Leu Glu His Thr Pro Val Tyr Thr Val Gly Ile Arg
            50                  55                  60

Ser Lys Gly Tyr Thr Lys Glu Glu Thr Arg Leu Met Arg Leu Gly
65                  70                  75                  80

Ala Glu Phe His Arg Thr Ser Arg Gly Gly Leu Ile Thr Phe His Gly
                85                  90                  95

Pro Gly Gln Leu Val Leu Tyr Pro Ile Cys Asp Val Arg Arg Ile Ser
                100                 105                 110

Ile Lys Gln Leu Gly Val Arg His Phe Val Asp Lys Leu Glu Gln Thr
                115                 120                 125

Ile Ile Asp Ala Ala Thr Glu Gly Phe Gly Ile Lys Asn Val Gly Arg
            130                 135                 140

Thr Ala Asn Thr Gly Val Trp Val Ser Asn Glu Arg Lys Leu Ala Ala
145                 150                 155                 160

Ile Gly Ile Ala Val Ser Gly Val Ser Tyr His Gly Ile Ala Ile
                165                 170                 175

Asn Cys Asn Thr Asp Leu Arg Trp Phe Asp Asn Ile Val Gly Cys Gly
                180                 185                 190

Ile Glu Gly Val Ser Thr Thr Ser Leu Ser Gln Glu Thr Ser Arg Asn
                195                 200                 205

Val Thr Val Ser Asp Ala Arg Pro Ile Leu Leu Asn Ala Phe Ala Asn
            210                 215                 220

Asn Phe Glu Cys Leu Leu Asn Glu Pro Asn Asp Tyr Ser Thr Cys Ser
225                 230                 235                 240

Asn Leu Lys Ile Thr Asn Val Val Ser Ser
                245                 250
```

```
<210> SEQ ID NO 25
<211> LENGTH: 2463
<212> TYPE: DNA
<213> ORGANISM: Homo sapiens
<220> FEATURE:
<221> NAME/KEY: CDS
<222> LOCATION: (1)..(2463)

<400> SEQUENCE: 25 atg aag atg tta ctc ctg ctg cat tgc ctt ggg gtg ttt ctg tcc tgt      48
Met Lys Met Leu Leu Leu Leu His Cys Leu Gly Val Phe Leu Ser Cys
1               5                   10                  15 tct gga cac atc cag gat gag cac ccc caa tat cac agc cct ccg gat     96
Ser Gly His Ile Gln Asp Glu His Pro Gln Tyr His Ser Pro Pro Asp
            20                  25                  30 gtg gtg att cct gtg agg ata act ggc acc aca aga ggc atg aca cct    144
Val Val Ile Pro Val Arg Ile Thr Gly Thr Thr Arg Gly Met Thr Pro
        35                  40                  45 cca ggc tgg ctc tcc tat atc ctg ccc ttt gga ggc cag aaa cac att    192
Pro Gly Trp Leu Ser Tyr Ile Leu Pro Phe Gly Gly Gln Lys His Ile
    50                  55                  60 atc cac ata aag gtc aag aag ctt ttg ttt tcc aaa cac ctc cct gtg    240
Ile His Ile Lys Val Lys Lys Leu Leu Phe Ser Lys His Leu Pro Val
65                  70                  75                  80 ttc acc tac aca gac cag ggt gct atc ctt gag gac cag cca ttt gtc    288
```

```
Phe Thr Tyr Thr Asp Gln Gly Ala Ile Leu Glu Asp Gln Pro Phe Val
                85                  90                  95 cag aat aac tgc tac tat cat ggt tat gtg gaa ggg gac cca gaa tcc      336
Gln Asn Asn Cys Tyr Tyr His Gly Tyr Val Glu Gly Asp Pro Glu Ser
            100                 105                 110 ctg gtt tcc ctc agt acc tgt ttt ggg ggt ttt caa gga ata tta cag      384
Leu Val Ser Leu Ser Thr Cys Phe Gly Gly Phe Gln Gly Ile Leu Gln
        115                 120                 125 ata aat gac ttt gct tat gaa atc aag ccc cta gca ttt tct acc acg      432
Ile Asn Asp Phe Ala Tyr Glu Ile Lys Pro Leu Ala Phe Ser Thr Thr
    130                 135                 140 ttt gaa cat ctg gta tac aag atg gac agt gag gag aaa caa ttt tca      480
Phe Glu His Leu Val Tyr Lys Met Asp Ser Glu Glu Lys Gln Phe Ser
145                 150                 155                 160 acc atg aga tcc gga ttt atg caa aat gaa ata aca tgc cga atg gaa      528
Thr Met Arg Ser Gly Phe Met Gln Asn Glu Ile Thr Cys Arg Met Glu
                165                 170                 175 ttt gaa gaa att gat aat tcc act cag aag caa agt tct tat gtg ggc      576
Phe Glu Glu Ile Asp Asn Ser Thr Gln Lys Gln Ser Ser Tyr Val Gly
            180                 185                 190 tgg tgg atc cat ttt agg att gtt gaa att gta gtc gtc att gat aat      624
Trp Trp Ile His Phe Arg Ile Val Glu Ile Val Val Val Ile Asp Asn
        195                 200                 205 tat ctg tac att cgt tat gaa agg aac gac tca aag ttg ctg gag gat      672
Tyr Leu Tyr Ile Arg Tyr Glu Arg Asn Asp Ser Lys Leu Leu Glu Asp
    210                 215                 220 cta tat gtt att gtt aat ata gtg gat tcc att ttg gat gtc att ggt      720
Leu Tyr Val Ile Val Asn Ile Val Asp Ser Ile Leu Asp Val Ile Gly
225                 230                 235                 240 gtt aag gtg tta tta ttt ggt ttg gag atc tgg acc aat aaa aac ctc      768
Val Lys Val Leu Leu Phe Gly Leu Glu Ile Trp Thr Asn Lys Asn Leu
                245                 250                 255 att gta gta gat gat gta agg aaa tct gtg cac ctg tat tgc aag tgg      816
Ile Val Val Asp Asp Val Arg Lys Ser Val His Leu Tyr Cys Lys Trp
            260                 265                 270 aag tcg gag aac att acg ccc cgg atg caa cat gac acc tca cat ctt      864
Lys Ser Glu Asn Ile Thr Pro Arg Met Gln His Asp Thr Ser His Leu
        275                 280                 285 ttc aca act cta gga tta aga ggg tta agt ggc ata gga gct ttt aga      912
Phe Thr Thr Leu Gly Leu Arg Gly Leu Ser Gly Ile Gly Ala Phe Arg
    290                 295                 300 gga atg tgt aca cca cac cgt agt tgt gca att gtt act ttc atg aac      960
Gly Met Cys Thr Pro His Arg Ser Cys Ala Ile Val Thr Phe Met Asn
305                 310                 315                 320 aaa act ttg ggc act ttt tca att gca gtg gct cat cat cta ggt cat     1008
Lys Thr Leu Gly Thr Phe Ser Ile Ala Val Ala His His Leu Gly His
                325                 330                 335 aat ttg ggc atg aac cat gat gag gat aca tgt cgt tgt tca caa cct     1056
Asn Leu Gly Met Asn His Asp Glu Asp Thr Cys Arg Cys Ser Gln Pro
            340                 345                 350 aga tgc ata atg cat gaa ggc aac cca cca ata act aaa ttt agc aat     1104
Arg Cys Ile Met His Glu Gly Asn Pro Pro Ile Thr Lys Phe Ser Asn
        355                 360                 365 tgt agt tat ggt gat ttt tgg gaa tat act gta gag agg aca aag tgt     1152
Cys Ser Tyr Gly Asp Phe Trp Glu Tyr Thr Val Glu Arg Thr Lys Cys
    370                 375                 380 ttg ctt gaa aca gta cac aca aag gac atc ttt aat gtg aag cgc tgt     1200
Leu Leu Glu Thr Val His Thr Lys Asp Ile Phe Asn Val Lys Arg Cys
385                 390                 395                 400
```

| | | |
|---|---|---|
| ggg aat ggt gtt gtt gaa gaa gga gaa gag tgt gac tgt gga cct tta<br>Gly Asn Gly Val Val Glu Glu Gly Glu Glu Cys Asp Cys Gly Pro Leu<br>                        405                        410                        415 | | 1248 |
| aag cat tgt gca aaa gat ccc tgc tgt ctg tca aat tgc act ctg act<br>Lys His Cys Ala Lys Asp Pro Cys Cys Leu Ser Asn Cys Thr Leu Thr<br>                   420                               425                        430 | | 1296 |
| gat ggt tct act tgt gct ttt ggg ctt tgt tgc aaa gac tgc aag ttc<br>Asp Gly Ser Thr Cys Ala Phe Gly Leu Cys Cys Lys Asp Cys Lys Phe<br>                  435                             440                        445 | | 1344 |
| cta cca tca ggg aaa gtg tgt aga aag gag gtc aat gaa tgt gat ctt<br>Leu Pro Ser Gly Lys Val Cys Arg Lys Glu Val Asn Glu Cys Asp Leu<br>450                              455                             460 | | 1392 |
| cca gag tgg tgc aat ggt act tcc cat aag tgc cca gat gac ttt tat<br>Pro Glu Trp Cys Asn Gly Thr Ser His Lys Cys Pro Asp Asp Phe Tyr<br>465                              470                             475                        480 | | 1440 |
| gtg gaa gat gga att ccc tgt aag gag agg ggc tac tgc tat gaa aag<br>Val Glu Asp Gly Ile Pro Cys Lys Glu Arg Gly Tyr Cys Tyr Glu Lys<br>                                 485                             490                        495 | | 1488 |
| agc tgt cat gac cgc aat gaa cag tgt agg agg att ttt ggt gca ggc<br>Ser Cys His Asp Arg Asn Glu Gln Cys Arg Arg Ile Phe Gly Ala Gly<br>                  500                               505                        510 | | 1536 |
| gca aat act gca agt gag act tgc tac aaa gaa ttg aac acc tta ggt<br>Ala Asn Thr Ala Ser Glu Thr Cys Tyr Lys Glu Leu Asn Thr Leu Gly<br>                  515                             520                        525 | | 1584 |
| gac cgt gtt ggt cac tgt ggt atc aaa aat gct aca tat ata aag tgt<br>Asp Arg Val Gly His Cys Gly Ile Lys Asn Ala Thr Tyr Ile Lys Cys<br>          530                             535                             540 | | 1632 |
| aat atc tca gat gtc cag tgt gga aga att cag tgt gag aat gtg aca<br>Asn Ile Ser Asp Val Gln Cys Gly Arg Ile Gln Cys Glu Asn Val Thr<br>545                              550                             555                        560 | | 1680 |
| gaa att ccc aat atg agt gat cat act act gtg cat tgg gct cgc ttc<br>Glu Ile Pro Asn Met Ser Asp His Thr Thr Val His Trp Ala Arg Phe<br>                         565                             570                        575 | | 1728 |
| aat gac ata atg tgc tgg agt act gat tac cat ttg ggg atg aag gga<br>Asn Asp Ile Met Cys Trp Ser Thr Asp Tyr His Leu Gly Met Lys Gly<br>                  580                               585                        590 | | 1776 |
| cct gat att ggt gaa gtg aaa gat gga aca gag tgt ggg ata gat cat<br>Pro Asp Ile Gly Glu Val Lys Asp Gly Thr Glu Cys Gly Ile Asp His<br>                        595                             600                        605 | | 1824 |
| ata tgc atc cac agg cac tgt gtc cat ata acc atc ttg aat agt aat<br>Ile Cys Ile His Arg His Cys Val His Ile Thr Ile Leu Asn Ser Asn<br>610                              615                             620 | | 1872 |
| tgc tca cct gca ttt tgt aac aag agg ggc atc tgc aac aat aaa cat<br>Cys Ser Pro Ala Phe Cys Asn Lys Arg Gly Ile Cys Asn Asn Lys His<br>625                              630                             635                        640 | | 1920 |
| cac tgc cat tgc aat tat ctg tgg gac cct ccc aac tgc ctg ata aaa<br>His Cys His Cys Asn Tyr Leu Trp Asp Pro Pro Asn Cys Leu Ile Lys<br>                         645                             650                        655 | | 1968 |
| ggc tat gga ggt agt gtt gac agt ggc cca ccc cct aag aga aag aag<br>Gly Tyr Gly Gly Ser Val Asp Ser Gly Pro Pro Pro Lys Arg Lys Lys<br>                  660                             665                        670 | | 2016 |
| aaa aag aag ttc tgt tat ctg tgt ata ttg ttg ctt att gtt ttg ttt<br>Lys Lys Lys Phe Cys Tyr Leu Cys Ile Leu Leu Leu Ile Val Leu Phe<br>                        675                             680                        685 | | 2064 |
| att tta tta tgt tgt ctt tat cga ctt tgt aaa aaa agt aaa cca ata<br>Ile Leu Leu Cys Cys Leu Tyr Arg Leu Cys Lys Lys Ser Lys Pro Ile<br>                  690                             695                        700 | | 2112 |
| aaa aag cag caa gat gtt caa act cca tct gca aaa gaa gag gaa aaa<br>Lys Lys Gln Gln Asp Val Gln Thr Pro Ser Ala Lys Glu Glu Glu Lys<br>705                              710                             715                        720 | | 2160 |

```
att cag cgt cga cct cat gag tta cct ccc cag agt caa cct tgg gtg      2208
Ile Gln Arg Arg Pro His Glu Leu Pro Pro Gln Ser Gln Pro Trp Val
                725                 730                 735 atg cct tcc cag agt caa cct cct gtg acg cct tcc cag agt cat cct      2256
Met Pro Ser Gln Ser Gln Pro Pro Val Thr Pro Ser Gln Ser His Pro
            740                 745                 750 cgg gtg atg cct tct cag agt caa cct cct gtg atg cct tcc cag agt      2304
Arg Val Met Pro Ser Gln Ser Gln Pro Pro Val Met Pro Ser Gln Ser
        755                 760                 765 cat cct cag ttg acg cct tcc cag agt caa cct cct gtg atg cct tcc      2352
His Pro Gln Leu Thr Pro Ser Gln Ser Gln Pro Pro Val Met Pro Ser
    770                 775                 780 cag agt cat cct cag ttg acg cct tcc cag agt caa cct cct gtg aca      2400
Gln Ser His Pro Gln Leu Thr Pro Ser Gln Ser Gln Pro Pro Val Thr
785                 790                 795                 800 ccc tcc cag agg caa cct cag ttg atg cct tcc cag agt caa cct cct      2448
Pro Ser Gln Arg Gln Pro Gln Leu Met Pro Ser Gln Ser Gln Pro Pro
                805                 810                 815 gtg acg ccc tcc tag                                                   2463
Val Thr Pro Ser
            820

<210> SEQ ID NO 26
<211> LENGTH: 820
<212> TYPE: PRT
<213> ORGANISM: Homo sapiens

<400> SEQUENCE: 26

Met Lys Met Leu Leu Leu His Cys Leu Gly Val Phe Leu Ser Cys
1               5                   10                  15

Ser Gly His Ile Gln Asp Glu His Pro Gln Tyr His Ser Pro Pro Asp
                20                  25                  30

Val Val Ile Pro Val Arg Ile Thr Gly Thr Thr Arg Gly Met Thr Pro
            35                  40                  45

Pro Gly Trp Leu Ser Tyr Ile Leu Pro Phe Gly Gly Gln Lys His Ile
        50                  55                  60

Ile His Ile Lys Val Lys Lys Leu Leu Phe Ser Lys His Leu Pro Val
65                  70                  75                  80

Phe Thr Tyr Thr Asp Gln Gly Ala Ile Leu Glu Asp Gln Pro Phe Val
                85                  90                  95

Gln Asn Asn Cys Tyr Tyr His Gly Tyr Val Glu Gly Asp Pro Glu Ser
                100                 105                 110

Leu Val Ser Leu Ser Thr Cys Phe Gly Gly Phe Gln Gly Ile Leu Gln
            115                 120                 125

Ile Asn Asp Phe Ala Tyr Glu Ile Lys Pro Leu Ala Phe Ser Thr Thr
        130                 135                 140

Phe Glu His Leu Val Tyr Lys Met Asp Ser Glu Glu Lys Gln Phe Ser
145                 150                 155                 160

Thr Met Arg Ser Gly Phe Met Gln Asn Glu Ile Thr Cys Arg Met Glu
                165                 170                 175

Phe Glu Glu Ile Asp Asn Ser Thr Gln Lys Gln Ser Ser Tyr Val Gly
            180                 185                 190

Trp Trp Ile His Phe Arg Ile Val Glu Ile Val Val Ile Asp Asn
        195                 200                 205

Tyr Leu Tyr Ile Arg Tyr Glu Arg Asn Asp Ser Lys Leu Leu Glu Asp
    210                 215                 220
```

-continued

```
Leu Tyr Val Ile Val Asn Ile Val Asp Ser Ile Leu Asp Val Ile Gly
225                 230                 235                 240

Val Lys Val Leu Leu Phe Gly Leu Glu Ile Trp Thr Asn Lys Asn Leu
            245                 250                 255

Ile Val Val Asp Asp Val Arg Lys Ser Val His Leu Tyr Cys Lys Trp
        260                 265                 270

Lys Ser Glu Asn Ile Thr Pro Arg Met Gln His Asp Thr Ser His Leu
    275                 280                 285

Phe Thr Thr Leu Gly Leu Arg Gly Leu Ser Gly Ile Gly Ala Phe Arg
290                 295                 300

Gly Met Cys Thr Pro His Arg Ser Cys Ala Ile Val Thr Phe Met Asn
305                 310                 315                 320

Lys Thr Leu Gly Thr Phe Ser Ile Ala Val Ala His His Leu Gly His
            325                 330                 335

Asn Leu Gly Met Asn His Asp Glu Asp Thr Cys Arg Cys Ser Gln Pro
        340                 345                 350

Arg Cys Ile Met His Glu Gly Asn Pro Pro Ile Thr Lys Phe Ser Asn
    355                 360                 365

Cys Ser Tyr Gly Asp Phe Trp Glu Tyr Thr Val Glu Arg Thr Lys Cys
370                 375                 380

Leu Leu Glu Thr Val His Thr Lys Asp Ile Phe Asn Val Lys Arg Cys
385                 390                 395                 400

Gly Asn Gly Val Val Glu Glu Gly Glu Glu Cys Asp Cys Gly Pro Leu
            405                 410                 415

Lys His Cys Ala Lys Asp Pro Cys Cys Leu Ser Asn Cys Thr Leu Thr
        420                 425                 430

Asp Gly Ser Thr Cys Ala Phe Gly Leu Cys Cys Lys Asp Cys Lys Phe
    435                 440                 445

Leu Pro Ser Gly Lys Val Cys Arg Lys Glu Val Asn Glu Cys Asp Leu
450                 455                 460

Pro Glu Trp Cys Asn Gly Thr Ser His Lys Cys Pro Asp Asp Phe Tyr
465                 470                 475                 480

Val Glu Asp Gly Ile Pro Cys Lys Glu Arg Gly Tyr Cys Tyr Glu Lys
            485                 490                 495

Ser Cys His Asp Arg Asn Glu Gln Cys Arg Arg Ile Phe Gly Ala Gly
        500                 505                 510

Ala Asn Thr Ala Ser Glu Thr Cys Tyr Lys Glu Leu Asn Thr Leu Gly
    515                 520                 525

Asp Arg Val Gly His Cys Gly Ile Lys Asn Ala Thr Tyr Ile Lys Cys
530                 535                 540

Asn Ile Ser Asp Val Gln Cys Gly Arg Ile Gln Cys Glu Asn Val Thr
545                 550                 555                 560

Glu Ile Pro Asn Met Ser Asp His Thr Thr Val His Trp Ala Arg Phe
            565                 570                 575

Asn Asp Ile Met Cys Trp Ser Thr Asp Tyr His Leu Gly Met Lys Gly
        580                 585                 590

Pro Asp Ile Gly Glu Val Lys Asp Gly Thr Glu Cys Gly Ile Asp His
    595                 600                 605

Ile Cys Ile His Arg His Cys Val His Ile Thr Ile Leu Asn Ser Asn
610                 615                 620

Cys Ser Pro Ala Phe Cys Asn Lys Arg Gly Ile Cys Asn Asn Lys His
625                 630                 635                 640

His Cys His Cys Asn Tyr Leu Trp Asp Pro Pro Asn Cys Leu Ile Lys
```

-continued

```
                    645                 650                 655
Gly Tyr Gly Gly Ser Val Asp Ser Gly Pro Pro Lys Arg Lys Lys
            660                 665                 670

Lys Lys Lys Phe Cys Tyr Leu Cys Ile Leu Leu Ile Val Leu Phe
        675                 680                 685

Ile Leu Leu Cys Cys Leu Tyr Arg Leu Cys Lys Lys Ser Lys Pro Ile
    690                 695                 700

Lys Lys Gln Gln Asp Val Gln Thr Pro Ser Ala Lys Glu Glu Lys
705                 710                 715                 720

Ile Gln Arg Arg Pro His Glu Leu Pro Pro Gln Ser Gln Pro Trp Val
            725                 730                 735

Met Pro Ser Gln Ser Gln Pro Pro Val Thr Pro Ser Gln Ser His Pro
            740                 745                 750

Arg Val Met Pro Ser Gln Ser Gln Pro Pro Val Met Pro Ser Gln Ser
            755                 760                 765

His Pro Gln Leu Thr Pro Ser Gln Ser Gln Pro Pro Val Met Pro Ser
        770                 775                 780

Gln Ser His Pro Gln Leu Thr Pro Ser Gln Ser Gln Pro Pro Val Thr
785                 790                 795                 800

Pro Ser Gln Arg Gln Pro Gln Leu Met Pro Ser Gln Ser Gln Pro Pro
            805                 810                 815

Val Thr Pro Ser
        820

<210> SEQ ID NO 27
<211> LENGTH: 2726
<212> TYPE: DNA
<213> ORGANISM: Mus musculus
<220> FEATURE:
<221> NAME/KEY: CDS
<222> LOCATION: (221)..(2512)

<400> SEQUENCE: 27
agaagctgtc ctgggcttct tggaggactc cttacatcat aagaaagaca atactaattt      60
aatactcaca tacctgtact tttatcatgg accaaaggaa tacagaccta aaggtttggc     120
acttccagag gacagatgca gtctagaagg attcagtcac tatgagtacc agttcttaat     180
tcttctttga atcaacattt ttataggagc cacatacata atg aat atg att gaa      235
                                               Met Asn Met Ile Glu
                                                 1               5 gca tta tta tcc atg aga gtc ttg ttc ctg aca caa gtg ttt ggg att      283
Ala Leu Leu Ser Met Arg Val Leu Phe Leu Thr Gln Val Phe Gly Ile
           10                  15                  20 ttc ctg tgt ttt cct gga ctc aca aag gct gga cat ctg cac tac cac      331
Phe Leu Cys Phe Pro Gly Leu Thr Lys Ala Gly His Leu His Tyr His
        25                  30                  35 agt tcc ata gaa gtg gtg att ccc atg aag gta act gag aaa acc aga      379
Ser Ser Ile Glu Val Val Ile Pro Met Lys Val Thr Glu Lys Thr Arg
    40                  45                  50 gga atg aac ctt cca aat tgg atc tcc tat agc ctt aaa ctt gga ggc      427
Gly Met Asn Leu Pro Asn Trp Ile Ser Tyr Ser Leu Lys Leu Gly Gly
55                  60                  65 cag aga tac atc atc cac atg aag atc aag aat ctt ttt cta acc agg      475
Gln Arg Tyr Ile Ile His Met Lys Ile Lys Asn Leu Phe Leu Thr Arg
70                  75                  80                  85 cac ctt cca gtg ttc acc tac tct gat cag gac tct ctg ctt gaa gat      523
His Leu Pro Val Phe Thr Tyr Ser Asp Gln Asp Ser Leu Leu Glu Asp
            90                  95                 100
```

-continued

| | |
|---|---|
| tac cct ttt gta cag gat gac tgc tac tac caa ggt tat gtg gag ggt<br>Tyr Pro Phe Val Gln Asp Asp Cys Tyr Tyr Gln Gly Tyr Val Glu Gly<br>105                110                    115 | 571 |
| gac tca gaa tca tta gtt tcc ctc agt tcc tgt ttt gga ggc ttt cat<br>Asp Ser Glu Ser Leu Val Ser Leu Ser Ser Cys Phe Gly Gly Phe His<br>120                125                    130 | 619 |
| gga cta tta gag ata aat aat att gtt tat gaa att atg ccc aag aag<br>Gly Leu Leu Glu Ile Asn Asn Ile Val Tyr Glu Ile Met Pro Lys Lys<br>135                140                    145 | 667 |
| ttt tct agg aaa ttt gaa cat ctg gtc tat aaa gtg gac att aat aaa<br>Phe Ser Arg Lys Phe Glu His Leu Val Tyr Lys Val Asp Ile Asn Lys<br>150                    155                    160                    165 | 715 |
| aca gaa tca agg ggt tcc agc ctt atg caa gat aac ata aca tgc caa<br>Thr Glu Ser Arg Gly Ser Ser Leu Met Gln Asp Asn Ile Thr Cys Gln<br>                    170                    175                    180 | 763 |
| gta gag tta caa aaa agt ggt aat ccc att ctc aag caa agt agt ttt<br>Val Glu Leu Gln Lys Ser Gly Asn Pro Ile Leu Lys Gln Ser Ser Phe<br>                    185                    190                    195 | 811 |
| gaa gac tgg tgg acc cat act aaa att gtt gaa tta gta gtg gtg gtg<br>Glu Asp Trp Trp Thr His Thr Lys Ile Val Glu Leu Val Val Val Val<br>                200                    205                    210 | 859 |
| gat aag act cta tat gac cac tat gga aat tat aca gta atg ctg tca<br>Asp Lys Thr Leu Tyr Asp His Tyr Gly Asn Tyr Thr Val Met Leu Ser<br>215                220                    225 | 907 |
| gat ctg tat tct gtg ata aat ata gtg gat acc att tat gag gta att<br>Asp Leu Tyr Ser Val Ile Asn Ile Val Asp Thr Ile Tyr Glu Val Ile<br>230                235                    240                    245 | 955 |
| ggt att aaa ata tta ttg gtt ggt gtg gag gtt tgg aat aag aaa aat<br>Gly Ile Lys Ile Leu Leu Val Gly Val Glu Val Trp Asn Lys Lys Asn<br>                    250                    255                    260 | 1003 |
| ctt att gtg ata gat gac gta agt aaa tct cta aga cta tat tgc cgg<br>Leu Ile Val Ile Asp Asp Val Ser Lys Ser Leu Arg Leu Tyr Cys Arg<br>                    265                    270                    275 | 1051 |
| tgg aaa gcc tca aac ttt ctt cat cgt tta aaa cat gat gtc tcg cat<br>Trp Lys Ala Ser Asn Phe Leu His Arg Leu Lys His Asp Val Ser His<br>                280                    285                    290 | 1099 |
| ctt ttc ata tat agg cac ttg aga gga tta agt ggc ata ggt tcc act<br>Leu Phe Ile Tyr Arg His Leu Arg Gly Leu Ser Gly Ile Gly Ser Thr<br>295                300                    305 | 1147 |
| ggg ggg att tgt gat cca aaa cgt agt tgt gca gtt gtt act ttc ata<br>Gly Gly Ile Cys Asp Pro Lys Arg Ser Cys Ala Val Val Thr Phe Ile<br>310                315                    320                    325 | 1195 |
| gac aga act ttg aac ctt cgt gcc att gga gtg gct cat cac tta ggt<br>Asp Arg Thr Leu Asn Leu Arg Ala Ile Gly Val Ala His His Leu Gly<br>                    330                    335                    340 | 1243 |
| cat aat ttg ggc atg aaa cat gat gaa gat ata tgt aag tgt agt tac<br>His Asn Leu Gly Met Lys His Asp Glu Asp Ile Cys Lys Cys Ser Tyr<br>                    345                    350                    355 | 1291 |
| agt aaa tgt ata atg cac atg gac agc cca ccg ata ccc aaa ttc agc<br>Ser Lys Cys Ile Met His Met Asp Ser Pro Pro Ile Pro Lys Phe Ser<br>                360                    365                    370 | 1339 |
| aat tgt agc tat aat tac ttt tgg tct tac act gta aag aac aca agg<br>Asn Cys Ser Tyr Asn Tyr Phe Trp Ser Tyr Thr Val Lys Asn Thr Arg<br>375                380                    385 | 1387 |
| tgt ttg atg gaa aac atg tac aca aag gat atc ttt gac agg aca cgc<br>Cys Leu Met Glu Asn Met Tyr Thr Lys Asp Ile Phe Asp Arg Thr Arg<br>390                395                    400                    405 | 1435 |
| tgt gga aat ggt gtt gtt gaa gac aaa gaa caa tgt gac tgt gga tca<br>Cys Gly Asn Gly Val Val Glu Asp Lys Glu Gln Cys Asp Cys Gly Ser | 1483 |

-continued

```
                   410                 415                 420
tta agg aat tgt aca aat gac ctt tgt tgc atg tca aac tgc act ctg    1531
Leu Arg Asn Cys Thr Asn Asp Leu Cys Cys Met Ser Asn Cys Thr Leu
        425                 430                 435 agt act ggg tct tcc tgt gcc ttt gga ctt tgc tgc aaa aac tgt cag    1579
Ser Thr Gly Ser Ser Cys Ala Phe Gly Leu Cys Cys Lys Asn Cys Gln
            440                 445                 450 ttt tta cca tca ggg act ctg tgt aga aaa agg gat aac att tgt gac    1627
Phe Leu Pro Ser Gly Thr Leu Cys Arg Lys Arg Asp Asn Ile Cys Asp
455                 460                 465 ctt cca gag tgg tgc aat ggg acg tcc cat gaa tgt cca gat gat gct    1675
Leu Pro Glu Trp Cys Asn Gly Thr Ser His Glu Cys Pro Asp Asp Ala
470                 475                 480                 485 tat gta gaa gat gga att ccc tgt ggg gtc tca gcc tat tgc tat gaa    1723
Tyr Val Glu Asp Gly Ile Pro Cys Gly Val Ser Ala Tyr Cys Tyr Glu
                490                 495                 500 aag caa tgt aat gac cgc aat gag cac tgt agg caa att ttt ggc cag    1771
Lys Gln Cys Asn Asp Arg Asn Glu His Cys Arg Gln Ile Phe Gly Gln
        505                 510                 515 aat gca aag act gca agt gta cat tgc tac aga gaa ata aac act aaa    1819
Asn Ala Lys Thr Ala Ser Val His Cys Tyr Arg Glu Ile Asn Thr Lys
            520                 525                 530 ggt gat cgt ttt ggc cat tgt ggt ctt cag gga cct act tac ata aaa    1867
Gly Asp Arg Phe Gly His Cys Gly Leu Gln Gly Pro Thr Tyr Ile Lys
535                 540                 545 tgt aaa agc aat gat gct ctt tgt gga aga att caa tgt gat aat gtg    1915
Cys Lys Ser Asn Asp Ala Leu Cys Gly Arg Ile Gln Cys Asp Asn Val
550                 555                 560                 565 gta caa att ccc aat atg aaa gat cac agt act att cac ttt gct ctt    1963
Val Gln Ile Pro Asn Met Lys Asp His Ser Thr Ile His Phe Ala Leu
                570                 575                 580 gtc aaa aat gta tct tgc tgg ggc act gat tac cac act ggg aca agc    2011
Val Lys Asn Val Ser Cys Trp Gly Thr Asp Tyr His Thr Gly Thr Ser
        585                 590                 595 cta act gat ata ggc gat gtg aaa gat ggc aca gag tgt gag caa aat    2059
Leu Thr Asp Ile Gly Asp Val Lys Asp Gly Thr Glu Cys Glu Gln Asn
            600                 605                 610 cat atc tgt atc aat agg cat tgt gta cat ata tct aca tta gac agc    2107
His Ile Cys Ile Asn Arg His Cys Val His Ile Ser Thr Leu Asp Ser
615                 620                 625 aac tgt aca cct gca ttc tgt aat tac agg ggc atc tgt aac aat aaa    2155
Asn Cys Thr Pro Ala Phe Cys Asn Tyr Arg Gly Ile Cys Asn Asn Lys
630                 635                 640                 645 cat cac tgc cac tgc aac ttc cac tgg gat cct cct aac tgt atg att    2203
His His Cys His Cys Asn Phe His Trp Asp Pro Pro Asn Cys Met Ile
                650                 655                 660 aga gga cat gga ggt agt gta gac agt ggc tta cct cct aaa aca aat    2251
Arg Gly His Gly Gly Ser Val Asp Ser Gly Leu Pro Pro Lys Thr Asn
        665                 670                 675 aaa aag aaa cat ttc ttc tat ctg ctt cta tta cag ctc att att ttg    2299
Lys Lys Lys His Phe Phe Tyr Leu Leu Leu Leu Gln Leu Ile Ile Leu
            680                 685                 690 gct tgc ctt tta agt tgt ctt ctt tgg cta ctt ttt aat ata aaa gga    2347
Ala Cys Leu Leu Ser Cys Leu Leu Trp Leu Leu Phe Asn Ile Lys Gly
695                 700                 705 agt aaa cga aag ccc caa gtt cag cct aca cct gta aaa aca aag aaa    2395
Ser Lys Arg Lys Pro Gln Val Gln Pro Thr Pro Val Lys Thr Lys Lys
        710                 715                 720                 725 gtt tca aag aaa gtt cca agc caa aaa ccg agt cca gtg cct tcc ccg    2443
```

```
Val Ser Lys Lys Val Pro Ser Gln Lys Pro Ser Pro Val Pro Ser Pro
                730                 735                 740 agt cta cct caa tta aga atg cca tca cga tct gct tca cca aca tca    2491
Ser Leu Pro Gln Leu Arg Met Pro Ser Arg Ser Ala Ser Pro Thr Ser
            745                 750                 755 tcc ata aaa agt acc aat taa atattaatca ttagtatggc tctccttgtt       2542
Ser Ile Lys Ser Thr Asn
        760 cttcatgatt ttaagtaata tgaagactgt tttctgtaat ttcgttcttt acatttccag  2602 aaaaaaataa tgtatgaata ggtattttc agattactgg ctatcagctt ttaatatttt   2662 atatactttg attgatattg caccatttct gctaaagcaa tcctcttcct atggggaaat  2722 agac                                                                2726
```

<210> SEQ ID NO 28
<211> LENGTH: 763
<212> TYPE: PRT
<213> ORGANISM: Mus musculus

<400> SEQUENCE: 28

```
Met Asn Met Ile Glu Ala Leu Leu Ser Met Arg Val Leu Phe Leu Thr
1               5                   10                  15

Gln Val Phe Gly Ile Phe Leu Cys Phe Pro Gly Leu Thr Lys Ala Gly
            20                  25                  30

His Leu His Tyr His Ser Ser Ile Glu Val Val Ile Pro Met Lys Val
        35                  40                  45

Thr Glu Lys Thr Arg Gly Met Asn Leu Pro Asn Trp Ile Ser Tyr Ser
    50                  55                  60

Leu Lys Leu Gly Gly Gln Arg Tyr Ile Ile His Met Lys Ile Lys Asn
65                  70                  75                  80

Leu Phe Leu Thr Arg His Leu Pro Val Phe Thr Tyr Ser Asp Gln Asp
                85                  90                  95

Ser Leu Leu Glu Asp Tyr Pro Phe Val Gln Asp Asp Cys Tyr Tyr Gln
            100                 105                 110

Gly Tyr Val Glu Gly Asp Ser Glu Ser Leu Val Ser Leu Ser Ser Cys
        115                 120                 125

Phe Gly Gly Phe His Gly Leu Leu Glu Ile Asn Asn Ile Val Tyr Glu
    130                 135                 140

Ile Met Pro Lys Lys Phe Ser Arg Lys Phe Glu His Leu Val Tyr Lys
145                 150                 155                 160

Val Asp Ile Asn Lys Thr Glu Ser Arg Gly Ser Ser Leu Met Gln Asp
                165                 170                 175

Asn Ile Thr Cys Gln Val Glu Leu Gln Lys Ser Gly Asn Pro Ile Leu
            180                 185                 190

Lys Gln Ser Ser Phe Glu Asp Trp Trp Thr His Thr Lys Ile Val Glu
        195                 200                 205

Leu Val Val Val Asp Lys Thr Leu Tyr Asp His Tyr Gly Asn Tyr
    210                 215                 220

Thr Val Met Leu Ser Asp Leu Tyr Ser Val Ile Asn Ile Val Asp Thr
225                 230                 235                 240

Ile Tyr Glu Val Ile Gly Ile Lys Ile Leu Val Gly Val Glu Val
                245                 250                 255

Trp Asn Lys Lys Asn Leu Ile Val Ile Asp Asp Val Ser Lys Ser Leu
            260                 265                 270

Arg Leu Tyr Cys Arg Trp Lys Ala Ser Asn Phe Leu His Arg Leu Lys
```

-continued

```
                275                 280                 285
His Asp Val Ser His Leu Phe Ile Tyr Arg His Leu Arg Gly Leu Ser
290                 295                 300

Gly Ile Gly Ser Thr Gly Ile Cys Asp Pro Lys Arg Ser Cys Ala
305                 310                 315                 320

Val Val Thr Phe Ile Asp Arg Thr Leu Asn Leu Arg Ala Ile Gly Val
                325                 330                 335

Ala His His Leu Gly His Asn Leu Gly Met Lys His Asp Glu Asp Ile
                340                 345                 350

Cys Lys Cys Ser Tyr Ser Lys Cys Ile Met His Met Asp Ser Pro Pro
                355                 360                 365

Ile Pro Lys Phe Ser Asn Cys Ser Tyr Asn Tyr Phe Trp Ser Tyr Thr
370                 375                 380

Val Lys Asn Thr Arg Cys Leu Met Glu Asn Met Tyr Thr Lys Asp Ile
385                 390                 395                 400

Phe Asp Arg Thr Arg Cys Gly Asn Gly Val Val Glu Asp Lys Glu Gln
                405                 410                 415

Cys Asp Cys Gly Ser Leu Arg Asn Cys Thr Asn Asp Leu Cys Cys Met
                420                 425                 430

Ser Asn Cys Thr Leu Ser Thr Gly Ser Ser Cys Ala Phe Gly Leu Cys
                435                 440                 445

Cys Lys Asn Cys Gln Phe Leu Pro Ser Gly Thr Leu Cys Arg Lys Arg
                450                 455                 460

Asp Asn Ile Cys Asp Leu Pro Glu Trp Cys Asn Gly Thr Ser His Glu
465                 470                 475                 480

Cys Pro Asp Asp Ala Tyr Val Glu Asp Gly Ile Pro Cys Gly Val Ser
                485                 490                 495

Ala Tyr Cys Tyr Glu Lys Gln Cys Asn Asp Arg Asn Glu His Cys Arg
                500                 505                 510

Gln Ile Phe Gly Gln Asn Ala Lys Thr Ala Ser Val His Cys Tyr Arg
                515                 520                 525

Glu Ile Asn Thr Lys Gly Asp Arg Phe Gly His Cys Gly Leu Gln Gly
530                 535                 540

Pro Thr Tyr Ile Lys Cys Lys Ser Asn Asp Ala Leu Cys Gly Arg Ile
545                 550                 555                 560

Gln Cys Asp Asn Val Val Gln Ile Pro Asn Met Lys Asp His Ser Thr
                565                 570                 575

Ile His Phe Ala Leu Val Lys Asn Val Ser Cys Trp Gly Thr Asp Tyr
                580                 585                 590

His Thr Gly Thr Ser Leu Thr Asp Ile Gly Asp Val Lys Asp Gly Thr
                595                 600                 605

Glu Cys Glu Gln Asn His Ile Cys Ile Asn Arg His Cys Val His Ile
610                 615                 620

Ser Thr Leu Asp Ser Asn Cys Thr Pro Ala Phe Cys Asn Tyr Arg Gly
625                 630                 635                 640

Ile Cys Asn Asn Lys His His Cys His Cys Asn Phe His Trp Asp Pro
                645                 650                 655

Pro Asn Cys Met Ile Arg Gly His Gly Gly Ser Val Asp Ser Gly Leu
                660                 665                 670

Pro Pro Lys Thr Asn Lys Lys His Phe Phe Tyr Leu Leu Leu Leu
                675                 680                 685

Gln Leu Ile Ile Leu Ala Cys Leu Leu Ser Cys Leu Leu Trp Leu Leu
                690                 695                 700
```

-continued

```
Phe Asn Ile Lys Gly Ser Lys Arg Lys Pro Gln Val Gln Pro Thr Pro
705                 710                 715                 720

Val Lys Thr Lys Lys Val Ser Lys Lys Val Pro Ser Gln Lys Pro Ser
                725                 730                 735

Pro Val Pro Ser Pro Ser Leu Pro Gln Leu Arg Met Pro Ser Arg Ser
            740                 745                 750

Ala Ser Pro Thr Ser Ser Ile Lys Ser Thr Asn
        755                 760

<210> SEQ ID NO 29
<211> LENGTH: 22
<212> TYPE: DNA
<213> ORGANISM: Artificial Sequence
<220> FEATURE:
<223> OTHER INFORMATION: Synthetic DNA

<400> SEQUENCE: 29
cagatgccct acaaagtctt cc                                          22

<210> SEQ ID NO 30
<211> LENGTH: 22
<212> TYPE: DNA
<213> ORGANISM: Artificial Sequence
<220> FEATURE:
<223> OTHER INFORMATION: Synthetic DNA

<400> SEQUENCE: 30
gccacggtgc catacagaga aa                                          22

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA

<400> SEQUENCE: 31
ggcaacccac caataactaa at                                          22

<210> SEQ ID NO 32
<211> LENGTH: 22
<212> TYPE: DNA
<213> ORGANISM: Artificial Sequence
<220> FEATURE:
<223> OTHER INFORMATION: Synthetic DNA

<400> SEQUENCE: 32
tcccacagcg cttcacatta aa                                          22
```

METHOD OF DIAGNOSIS/PROGNOSIS OF HUMAN CHRONIC LYMPHOCYTIC LEUKEMIA COMPRISING THE PROFILING OF *LPL/ADAM* GENES

BACKGROUND OF THE INVENTION

1. Field of the Invention

The present invention provides methods of diagnosis and prognosis of human chronic lymphocytic leukemia (CLL) in a subject a patient in need thereof. The methods of the present invention involve measuring the expression profile of two known genes: LPL and ADAM29; and determining the ratio of their expression to diagnose the presence of CLL or to prognose the likelihood of developing CLL, an aggressive or a stable form of the disease or the symptoms consistent with CLL.

2. Discussion of the Background

Chronic lymphocytic leukemia (CLL) displays a variable outcome. The classical Rai[1] or Binet[2] staging systems have allocated CLL cases into three major risk groups (low [stage 0 in Rai's and stage A in Binet's classification system], intermediate [stages I and II in Rai's and stage B in Binet's classification system], and high [stage III and IV in Rai's and stage C in Binet's classification system]), according to tumor burden and the presence of anemia and thrombocytopenia. These staging systems have provided a basis for therapeutic stratification. Asymptomatic patients with a low tumor burden (Binet stage A) do not benefit from treatment with chlorambucil. However, the disease in half of these patients will progress and both staging systems fail to initially identify such patients. The advent of new treatments such as purine analogues and monoclonal antibodies directed against CD20 and CD52 are able to induce complete remissions and may allow early treatment for asymptomatic patients whose disease is likely to progress.[3] Accurate identification of these patients is therefore increasingly important.

Serologic markers such as lactic dehydrogenase, beta2-microglobulin[4], soluble CD23[5] and thymidine kinase[4,6] are essentially indicators of disease activity and/or load, although some can anticipate disease progression[7]. Phenotypic expression of CD38 has been associated with aggressive disease[8], but the threshold level for positive cases, if it exists at all, remains a matter of debate.[9-11] Genomic aberrations correlate well with either good (isolated 13q$^-$) or poor (17p$^-$; 11p$^-$) prognosis in CLL[10,12,13], though their occurrence as a second malignant hit cannot be definitely excluded.

The mutational status of immunoglobulin heavy chain variable (IgVH) genes has been considered as the best prognostic marker in CLL. In an initial study, the present inventors observed that at least half of CLL cases carried mutations using a cut-off of 98% germline homology.[14] This was further confirmed by others,[15] some of which also correlated the IgVH mutational status to clinical behavior.[8,16,17] Mutated (MT) patients usually demonstrate a favorable evolution when compared to unmutated (UM) cases ($\geq$98% germline homology), which are characterized by progressive disease, continuing treatment needs and a high proportion of CLL-related deaths. This analysis remains costly, time-consuming and inaccessible for most medical facilities. Consequently, the detection of appropriate, reliable surrogate markers for IgVH mutational status has retained worldwide attention.

CD38 was the first candidate proposed to replace IgVH sequencing,[8] with positive and negative cases corresponding respectively to UM and MT patients, but finally demonstrated insufficient specificity (about 30% discordance for each group).[11] In addition, its expression can vary during the course of disease.[11] Surprisingly, recent reports indicated that ZAP-70 mRNA, normally expressed in T and NK lymphocytes, is also transcribed in CLL B-cells lacking IgVH mutations.[18,19] Two further series have confirmed these findings at the protein level,[20,21] suggesting a pivotal role for ZAP-70 in prediction of IgVH mutational status. There is however some controversy to whether ZAP-70 is really a good surrogate marker since two recent reports failed to demonstrate a significant concordance between its expression and the degree of somatic mutation in the IgVH genes.[22,23]

Accordingly, there remains a critical need for a safe, inexpensive and accurate means to diagnose CLL and prognostic methods involving the same.

To address this need, in a study of gene expression profiling performed on 18 CLL cases, the present inventors identified a limited set of genes (n=85), which were expressed differentially between progressive UM and stable MT CLLs (Vasconcelos, et al., manuscript submitted July 2004). These results were validated by real-time quantitative polymerase chain reaction (RQ-PCR) for 18 genes on the same cDNAs that were hybridized on the DNA chips. From these RQ-PCR experiments, 4 genes in addition to ZAP-70 appeared to provide a better segregation of the 2 groups of CLLs. They included the lipoprotein lipase (LPL) and spartin (SPG20) genes, whose expression was higher in UM patients, while a disintegrin and metalloproteinase 29 (ADAM29) and nuclear receptor-interacting protein 1 (NRIPI) genes were found at much higher levels in MT cases. These findings led the present inventors to investigate, in an independent and larger CLL series, which of these 4 genes (isolated or in combination) could represent the best surrogate marker for IgVH mutational status, and how they would compare to ZAP-70 protein expression.

SUMMARY OF THE INVENTION

It is an object of the present invention to provide a method of identifying a subject suspected of having a lymphocytic leukemia by determining the gene expression levels of LPL and ADAM29 in a sample obtained from a subject; and comparing the expression levels to a standard expression level of the corresponding genes in a normal subject. In this method, the gene expression level is determined by measuring mRNA, cDNA or protein expression level.

It is an object of the present invention to provide a method of identifying a subject with a significant probability of having lymphocytic leukemia in a subject in need thereof by determining the gene expression levels of LPL and ADAM29 in B cells and designating the subject as having a significant probability of having chronic lymphocytic leukemia expression of at least one of LPL and ADAM29 is detected in said B cells. In this object and those that follow, B-cells may be obtained from any source that contains the same, including: peripheral mononuclear blood cells, tissues naturally bearing B-cells such as backbone, ganglions, spleen, mucosa, and skin, or tissues in which B-cells do not naturally reside, such as a tissue has been infiltrated by malignant (tumor) cells.

Further, the above object may be performed using a sample containing previously extracted mRNA (e.g., a mRNA bank), thereby obviating the need to obtain a cellular sample and, thus, an object of the present invention includes a method of identifying a subject with a significant probability of having chronic lymphocytic leukemia in a subject in need thereof by determining the gene expression levels of LPL and ADAM29 in a sample containing mRNA and designating the subject as having a significant probability of having chronic lymphocytic leukemia expression of at least one of LPL and ADAM29 is detected in said sample.

It is another object of the present invention to provide a predictive method for determining the mutational status of the IgVH genes classifying said IgVH mutational status of a subject by evaluating the LPL/ADAM29 gene expression ratio in a sample containing mRNA; and classifying the IgVH gene on the basis of this ratio. In this object of the present invention, the sample containing mRNA may be either cellular (e.g., a peripheral blood) or previously extracted (e.g., a mRNA bank).

It is another object of the present invention to validate the classification of the disease based on IgVH mutational status determined by the LPL/ADAM29 gene expression ratio by either: (a) direct sequencing of the IgVH genes, or (b) by determining the percentage of CD19+ CD3− CD56− lymphoid cells present in a peripheral blood sample that are positive for ZAP-70 intracellular expression.

Yet another object of the present invention is to provide a method of classifying IgVH mutational status of a subject having chronic lymphocytic leukemia by performing a competitive multiplex PCR assay to determine the preferential expression of LPL and ADAM29.

Still another object of the present invention is to provide a prognostic method to determine event free survival of a subject having chronic lymphocytic leukemia.

The present invention provides a method of allowing accurate estimation of the prognosis in a patient having chronic lymphocytic leukemia, by designating the subject as having a significant probability of having an aggressive form of the disease if there is overexpression of the LPL gene or an indolent form of the disease if there is overexpression of ADAM29 gene.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

(A) The lymphocyte population was first gated (region R1) on forward and side scatter histogram (left). The CLL cells (CD-19+) were then selected (gate R2), as well as the T cell (CD3+) and NK (CD-56+) populations (gate R3), as shown on right side histogram. (B) and (D) Biparametric plots of ZAP-70 or isotype-match control antibody (CD14) expression on different cell populations. The level of expression of ZAP-70 on T and NK cells (middle plots) served to determine a threshold, which was then used to quantify its expression on B cells (right plots). Left plots show the absence of fixation of the isotype-match control antibody on lymphocytes. (C) and (E) Monoparametric histograms of ZAP-70 or isotype-match control antibody (CD14) expression on different cell populations. The light and dark gray histograms correspond to B and NK cell staining respectively. The black overlaid histogram shows the absence of fixation of the isotype-match control antibody on lymphocytes. Expression of ZAP-70 on CD3+ CD56+ cells (M1) served to determine the percentage of CLL cells that were positive for ZAP-70. The percentage of B cells expressing ZAP-70 is indicated. (B) and (C) panels illustrate a ZAP-70 negative CLL case, while panels (D) and (E) show a ZAP-70 positive case. Abbreviations: B, B cell; T, T cell; NK, natural killer; IC, isotype-matched control.

Figure 2:
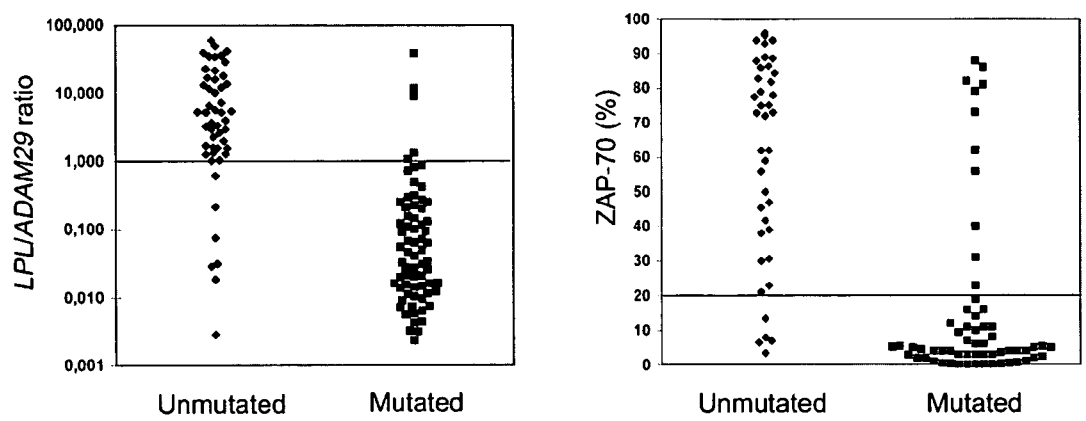

FIG. 2. Correlations between LPL/ADAM29 ratio or ZAP-70 expression and the IgVH gene mutational status.

The threshold values calculated for the L/A ratio (=1) and ZAP-70 (=20%) showing the best concordance rate with the IgVH mutational status, as determined by using Youden's index, are indicated by a horizontal line.

Figure 3:
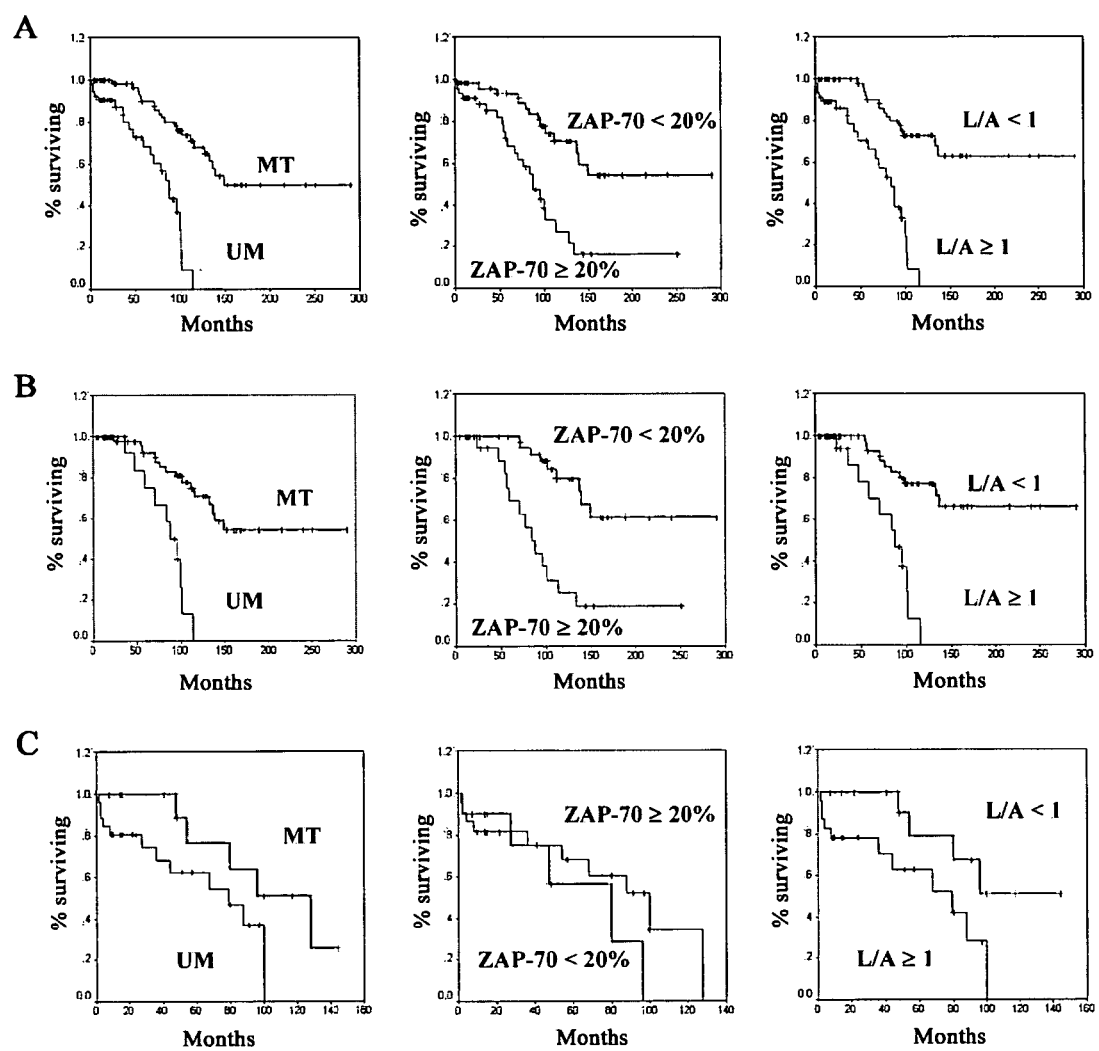

FIG. 3. Kaplan-Meier survival curves in CLL according to IgVH mutational status, L/A ratio or ZAP-70 expression.

(A) Event-free survival probabilities for the total population. (B) Event free survival probabilities for stage A patients. (C) Overall survival probabilities for stage B and C patients.

Figure 4:
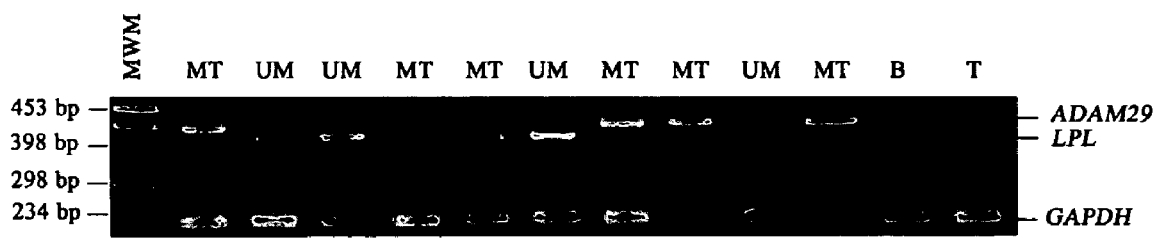

FIG. 4. Multiplex PCR determination of LPL and ADAM29 expression.

LPL and ADAM29 transcripts were amplified simultaneously, the PCR products were then separated by electrophoresis on agarose gel and visualised under UV illumination after ethidium bromide staining. Amplification of the GAPDH gene from the same transcripts served as control of cDNA integrity. MWM indicates molecular weight marker, MT, mutated; UM, unmutated; B, purified B cells from a healthy individual; T, Jurkatt T-cell line.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The state of the oncological arts suggests that chronic lymphocytic leukemia (CLL) patients expressing mutated (MT) IgVH genes display good prognosis when compared to patients expressing unmutated (UM) IgVH genes. However, heretofore, it has been difficult and costly to extend this study to routine practice. As such, there is a strong need for surrogate markers to distinguish IgVH status and, thus, prognostic indicators for CLL patients.

ZAP-70 has been shown to be overexpressed in patients displaying UM IgVH genes. The speculation that ZAP-70 gene expression could differentiate MT from UM CLLs has emerged from microarray experiments,[18,19] and was further confirmed at the protein level by flow cytometry.[20,21] In the examples of the present invention, the present inventors evaluated ZAP-70 expression in CLL cases. The threshold value which best correlated with the IgVH mutational status was found to be 20%, similar to that described by Crespo et al.,[20] but higher than that used by Orchard et al. (10%).[21] Discordant results were obtained in 16% of patients, a rate slightly higher than that observed with the L/A ratio (10%; see below), and occurred more frequently among MT CLLs (10%) than UM CLLs (5%). This level of discordance was also higher than that reported by the 2 aforementioned studies (respectively 5.4% and 7.8%). Both reports identified ZAP-70 negative cases with UM IgVH genes, some of which had an apparently stable disease, similarly to the present inventors' findings. Conversely, Orchard et al. described ZAP-70 positive cases with MT IgVH genes, although all had a 96%-

97% homology.[21] In contrast 4 of the patients described below in this group expressed IgVH genes with less than 95% homology, with 3 of them having a stable disease. Therefore a clear dissociation between ZAP-70 expression and IgVH mutational status exists within a subset of patients, thus indicating that ZAP-70 alone is an insufficient surrogate marker for CLL prognosis.

The recent development of microarray technology has allowed the discovery of genes, which may have prognostic significance in human tumors. A previous gene expression profiling study in CLL led the present inventors to identify 4 genes that appeared to best segregate stable MT from progressive UM forms (Vasconcelos, et al., manuscript submitted July 2004). LPL and SPG20 were expressed preferentially UM CLL, while ADAM29 and NRIP1 had a predominant expression in MT CLL.

As described herein, the present inventors have monitored the expression levels of these genes on a large series of CLL patients and evaluated the correlation with the IgVH mutational status and clinical outcome. Both LPL and ADAM29 were found to correlate better with the IgVH mutational status than SPG20 and NRIP1. Even better results were obtained when combining LPL and ADAM29 by a simple ratio of their normalized expression values, reaching 90% concordance. The L/A ratio thus constitutes a suitable surrogate marker of the IgVH mutational status in CLL.

LPL is a heparin-releasable enzyme bound to glycosaminoglycan components of the capillary endothelium, and is particularly abundant in muscle, adipose tissue and macrophages. As used in the context of the present invention LPL is preferably the human sequence (gene=SEQ ID NO: 11; protein=SEQ ID NO: 12). LPL is also known to exist in the following organisms: *Rattus norvegicus* (UniGene Rn.3834; gene sequence=SEQ ID NO: 13; protein sequence=SEQ ID NO: 14), *Mus musculus* (UniGene Mm.1514; gene sequence=SEQ ID NO: 15; protein sequence=SEQ ID NO: 16), *Gallus gallus* (UniGene Gga.1152; gene sequence=SEQ ID NO: 17; protein sequence=SEQ ID NO: 18), *Canis familiaris* (UniGene Cfa.3489; gene sequence=SEQ ID NO: 19; protein sequence=SEQ ID NO: 20), *Bos Taurus* (UniGene Bt.5387; gene sequence=SEQ ID NO: 21; protein sequence=SEQ ID NO: 22), and *Caenorhabditis elegans* (UniGene Cel. 18189; gene sequence=SEQ ID NO: 23; protein sequence=SEQ ID NO: 24). With apolipoprotein CII, LPL mediates the hydrolysis of triacylglycerol component of circulating chylomicrons and very low-density lipoproteins. It plays a central role in lipid metabolism and transport.[29,30] Mutations in the LPL gene are frequently associated with dyslipidemia and atherosclerosis.[29,31] In line with the present inventors findings on normal cells, other investigators have failed to detect LPL expression in normal purified B and T lymphocytes.[32] However, they found that it was expressed and secreted by NK cells, where it was shown to modulate their cytotoxic activity. Reasons for its high expression in UM CLL B-cells are unknown.

The ADAM29 gene encodes a member of the disintegrin and metalloprotease family of transmembrane proteins, which have been shown to mediate cell-cell and/or cell-matrix interactions as well as the proteolytic shedding of cell surface molecules.[33,34] In contrast to other ADAMs that are expressed in various tissues, ADAM29 transcripts are highly restricted to the testis.[35] The origin of ADAM29 over-expression in MT CLL B cells remains speculative. As used in the context of the present invention ADAM29 is preferably the human sequence (gene=SEQ ID NO: 25; protein=SEQ ID NO: 26). ADAM29 is also known to exist in the following organisms: *Mus musculus* (UniGene Mm.67684; gene sequence=SEQ ID NO: 27; protein sequence=SEQ ID NO: 28).

The present invention also embraces the following LPL and ADAM29 gene sequences.

LPL: Hs. 180878 (UniGene)
   NM 000237 (RefSeq)
ADAM29: Hs.126838 (UniGene) and
   NM 014269 (RefSeq)=variant 1
   NM 021780 (RefSeq)=variant 2
   NM 021779 (RefSeq)=variant 3

Primers that may be used to amplify these sequences include:

```
                                    (SEQ ID NO: 29)
LPL (CS)s         CAGATGCCCTACAAAGTCTTCC (SEQ ID NO: 30)
LPL (CS)as        GCCACGGTGCCATACAGAGAAA (SEQ ID NO: 31)
ADAM29 (CS)s      GGCAACCCACCAATAACTAAAT (SEQ ID NO: 32)
ADAM29 (CS)as     TCCCACAGCGCTTCACATTAAA
```

All three ADAM29 variants can be amplified by the aforementioned primers.

The fact that for these 2 genes: i) similar results were obtained on total CLL lymphocyte populations and from purified leukemic cells, and ii) their absence of detection or very low level in normal B cells, indicates that their expression could to be tumor specific. Alternatively it might reflect a restricted expression in a minor B lymphoid subpopulation which is expanded in CLL. Therefore, contemplated by the present invention are methods in which a threshold B-cell expression level of the aforementioned genes can be determined for CLL positive diagnosis.

Accordingly, in an embodiment of the present invention is to provide a method of identifying a subject with a significant probability of having chronic lymphocytic leukemia in a subject in need thereof by:

obtaining a specimen from said subject, wherein said specimen comprises at least one of peripheral mononuclear blood cells (PBMC), tissue containing B-cells, and extracted B cells;

determining the gene expression levels of LPL and ADAM29 in said specimen;

designating said subject as having a significant probability of having chronic lymphocytic leukemia if said determining evidence expression of at least one of LPL and ADAM29 in said specimen.

In the embodiments of the present invention described herein, B-cells may be obtained from any source that contains the same, including: peripheral mononuclear blood cells, tissues naturally bearing B-cells such as backbone, ganglions, spleen, mucosa, and skin, or tissues in which B-cells do not naturally reside, such as a tissue has been infiltrated by malignant (tumor) cells.

Further, the above embodiment may be performed using a sample containing previously extracted mRNA (e.g., a mRNA bank), thereby obviating the need to obtain a cellular sample and, thus, an embodiment of the present invention includes a method of identifying a subject with a significant probability of having chronic lymphocytic leukemia in a subject in need thereof, by obtaining a sample containing mRNA, wherein said sample contains at least one selected from the group consisting of extracted mRNA, peripheral mononuclear blood cells (PBMC), tissue containing B-cells, and extracted B cells;

determining the gene expression levels of LPL and ADAM29 in said sample;

designating said subject as having a significant probability of having chronic lymphocytic leukemia if said determining evidence expression of at least one of LPL and ADAM29 in said sample.

An advantage offered by the aforementioned embodiments is that the present invention may be utilized to detect leukemias in patients in which all the other common leukemia markers are "silent." In these particular cases, the ratio L/A will become the only available diagnostic method. As such, the present invention embraces a general diagnostic method comprising identifying a subject having a significant probability of having chronic lymphocytic leukemia comprising determining the L/A ratio in a sample obtained from said subject by the methods described herein.

As used herein, the term "significant probability" in the phrase "having a significant probability of having chronic lymphocytic leukemia" is defined as being a greater 80%, preferably greater than 85%, more preferably greater than 90%, most preferably greater than 95% chance that said subject has CLL. As shown in the examples of the present specification, the LPL and ADAM29 gene expression levels of 134 subjects were evaluated: 127 pre-diagnosed as having CLL and 7 healthy subjects. Of these only one healthy patient exhibited any expression of LPL or ADAM29 in either PBMC or B cells (low levels of LPL in B cells), corresponding to no less than 85.7% accuracy in CLL diagnosis, and all pre-diagnosed CLL patients expressed LPL or ADAM29 in either PBMC or B cells, corresponding to an accuracy in the overall population of greater than 99%.

As used herein the phrase "aggressive form of chronic lymphocytic leukemia" means that subjects present, in addition to an abnormal hemogram, clinical symptoms such as an important tumor mass and/or cytopenia such as anemia or trombopenia.

As used herein the phrase "indolent form of chronic lymphocytic leukaemia" means that subjects present an anormal hemogram; however, do not presentany clinical symptom normally associated with the disease. At this stage, the disease is only detectable by labs means.

As used herein, the phrase "subject in need thereof" is defined as a subject that is suspected of having CLL or has been independently (e.g., by conventional CLL diagnostic methods) diagnosed as suffering from CLL. Of course, it is contemplated that the present invention may be extended to routine preventative medical practices. For example, it is to be understood that the present invention may be used with "healthy" subjects as a part of a routine physical examination.

Further, as used in the context of the present invention, the term "subject" is defined as including any animal that expresses LPL and ADAM29. In a preferred embodiment the "subject" is a human. Further, it should be noted that the term "patient" is used herein interchangeably with the term "subject." In view of the fact that CLL has been found to occur in bovine, the present invention may find application in animals that possess both an LPL gene and an ADAM29 gene.

As used herein, the terms "specimen" or are defined as being any extracted biological material in which cellular material of blood is likely to be found. As used herein the term "sample" is defined as being any biological material naturally occurring or extracted in which cellular or genetic (i.e., mRNA) is contained. In an embodiment of the present invention, these terms refer to peripheral blood samples, tissue containing B cell, or extracted B cells. Within the context of the present invention, the specimen or sample may be used in a crude form, a preserved form (i.e., includes additional additives commonly added to preserve the integrity of the cellular material under environmental stress, such as freezing), a partially purified form, a purified form (e.g., isolated cellular material), or any other common preparatory form.

In the methods of the present invention, it is to be understood that any common (i.e., standard) method of acquiring biological specimens may be employed. These methods are readily appreciated by the skilled clinician and need not be described in great detail.

Within the context of the present invention, the gene (and/or protein) expression levels of the genes (and/or proteins) discussed herein is not particularly limited. Gene expression may be determined by any quantitative, semi-quantitative or qualitative method including PCR methods. Specific PCR methods that are suitable for use in the present invention include real-time PCR (RQ-PCR) multiplex-PCR and fluorescent MX-PCR. It is also understood that microarray techniques may be employed to provide quantitative values for gene expression. Protein expression is preferentially determined by flow cytometry.

Appropriate quantification methods requiring labelling of mRNA or DNA has been described in WO93/10257, U.S. Pat. Nos. 5,747,246, 5,955,262, and 5,876,928 (Kourilsky et al.), which are incorporated herein by reference. Protein quantification may be also accomplished by using directly or indirectly labelled polyclonal or monoclonal antibodies specifically directed against each of one expressed protein LPL or ADAM29.

Labelled proteins could be detected directly on cells either by cytometric techniques (cell-shorter techniques, cellular suspensions, etc.) or by histochemical techniques (fixed cells, solid or semi-solid tissues). Cells could be previously permeabilized to allow the introduction into the B-cell cytoplasma of the appropriate antibody. Also labelled proteins may be extracted outside the cells and analyzed by Western blot techniques, after migration of the cell extracts on Polyacrylamide gels (PAGE-SDS).

Further, the present invention also contemplates methods in which relative expression levels are determined for LPL and ADAM29. For example, to determine the LPL/ADAM29 ratio, it is possible to employ a simple electrophoretic technique in which PCR products are separated by electrophoreses and the relative intensities of the bands corresponding to LPL (approximately 410 bp for humans) and ADAM29 (approximately 445 bp for humans) is determined. Such a technique is readily amendable to RQ-PCR and multiplex PCR platforms.

However, as used in the present invention, the gene expression level of LPL and ADAM29 is preferably a normalized gene expression, which is preferably obtained by RQ-PCR (real-time polymerase chain reaction) using the Light Cycler System (Roche Molecular Biochemicals, Mannheim, Germany) and the SYBR Green I dye. As evidenced below under the heading "Quantitative RT-PCR" gene expression analyses was conducted for LPL, SPG20, ADAM29 and NRIP1; however, the technique described herein may be extended to gene expression of any gene of interest.

In a preferred embodiment, primers are designed to be specific for the gene of interest and RQ-PCR is performed with a predetermined quantity (e.g., 100-150 ng) of reverse transcribed total RNA (cDNA) for a time and under conditions suitable for amplifying the gene of interest from the reverse transcribed total RNA (cDNA). For example, the conditions may entail: 10 minutes at 95° C. for initial denaturation, then 40 cycles of 10 seconds at 95° C., 5 seconds at 62°

C. and 17 seconds at 72° C. The specificity of the amplified products is then preferably verified by analysis of their respective melting curves.

By repeating the procedure in duplicate and by including the 5 points of the calibration curve and a no-template control in each PCR reaction, the results may be validated. Estimation of the quality of cDNA for each sample is preferably obtained by quantification of an endogenous reference. In one embodiment of the present invention, the endogenous reference is the glyceraldehyde-3-phosphate dehydrogenase (GAPDH). GAPDH gene has been used in the present invention as a housekeeping gene, but normalization may also be performed by using any other housekeeping gene. Examples of genes that are suitable for use as normalization genes in quantitative PCR techniques include, but are not limited to:

18S rRNA (ARN ribosomal 18S)
ABL (Abelson)
PO (Acidic ribosomal protein)
ACTB (Beta-actin)
B2M (Beta-2-microglobulin)
GUS (Beta-Glucuronidase)
CYC (Cyclophilin)
GAPDH (Glyceraldehyde 3 phosphate dehydrogenase)
HPRT (Hypoxanthine phosphoribosyltransferase)
PGK (Phosphoglycerokinase)
PBGD (Porphobilinogen deaminase)
PBGD2 (Porphobilinogen deaminase 2)
TBP (transcription factor IID)
TFRC (Transferrin receptor)

To this end, the artisan is referred to Beillard et al., Leukemia, 2003, 17, 2474-2486 (which is incorporated herein by reference), for information relevant to the use of the foregoing as normalization genes in quantitative PCR techniques.

Once the foregoing is complete, the gene copy number is preferably calculated using a standard curve generated from serially diluted (10-fold dilutions from $10^6$ to $10^2$ copies) plasmids containing the respective sequence verified insert (LPL, ADAM29, Housekeeping gene, etc.). Results are expressed as the ratio of mean of gene copy number/mean GAPDH copy number×100 (used herein as "normalized gene expression").

Accordingly, as used herein, when the term "gene expression level" preferably means that the expression level has been quantitatively determined and is normalized. To facilitate gene expression level determination, it is preferred that total cellular RNA is extracted from the sample from the subject under study and that the corresponding cDNA be synthesized to serve as a PCR template.

A microarray study by the present inventors showed overexpression of LPL and ADAM29 genes among UM and MT CLLs, respectively. The present inventors quantified expression of LPL and ADAM29 genes by RQ-PCR, and ZAP-70 protein by flow-cytometry in a cohort of 127 CLL patients, and evaluated the correlations with the IgVH mutational status and clinical outcome. Combining LPL and ADAM29 mRNA quantifications by a simple 1 to 1 ratio (L/A ratio) provided a 90% concordance rate with the IgVH mutational status. Simultaneous usage of the L/A ratio and ZAP-70 expression allowed an almost perfect (99%) assessment of the IgVH status in the 80% of patients with concordant results (L/A$^+$, ZAP-70$^+$ or L/A$^-$, ZAP-70$^-$). IgVH mutational status, ZAP-70 and the L/A ratio were predictive of event-free survival for the whole cohort and for stage A patients. In addition the L/A ratio was an independent pronostic factor for stage B and C patients.

Accordingly, in another embodiment of the present is to provide a method of classifying IgVH mutational status of a subject having chronic lymphocytic leukemia by obtaining a sample containing mRNA from said subject (preferably a peripheral blood sample, a tissue sample, or extracted B cells from said subject or pre-extracted mRNA from said subject);
determining the gene expression levels of LPL and ADAM29 in said sample;
evaluating the LPL/ADAM29 gene expression ratio; and
classifying the IgVH gene as:
mutated if the LPL/ADAM29 ratio is less than one, or
unmutated if the LPL/ADAM29 ratio is greater than or equal to one.

In this embodiment, the subject in need of classifying IgVH mutational status may be either a subject that has been diagnosed by conventional methods as having CLL or may be a subject that has been identified as having a significant probability of having CLL by the method described hereinabove.

If the L/A ratio or ZAP-70 (described in the art previously) would be used independently as surrogate marker of the mutational status, it may lead to an inappropriate classification of a small fraction of patients, which may be problematic in a risk-adapted therapeutic attitude. Therefore, in an embodiment of the present invention, the present inventors therefore combined both markers, which resulted in a much closer correlation with the IgVH mutational status.

To this end, the ZAP-70 expression level may be determined as described previously[20,21] or by the method detailed in the Examples of the present specification. The ZAP-70 expression level is then used in the context of the present invention to validate the IgVH mutational status classified by the L/A ratio. To this end, the validation method is conducted by:

determining the percentage of CD3+ CD56+ cells present in a specimen from the subject classified by L/A ratio that are positive for ZAP-70 intracellular expression; and
classifying the IgVH gene sequence as:
mutated if the percentage of CD19+ CD3− CD56-cells present in said specimen that are positive for ZAP-70 intracellular expression is less than 20%, or
unmutated if the percentage of CD19+ CD3− CD56− cells present in said specimen that are positive for ZAP-70 intracellular expression is greater than or equal to 20%.

In the Examples of the present specification, all but one of the 74 cases expressing concordant ZAP-70 and L/A ratio were correctly assigned to their mutational group. Conversely, in about 20% of cases, ZAP-70 and the L/A ratio gave discordant results. Therefore, combining ZAP-70 and L/A ratio quantification represents an alternative to sequencing the IgVH genes in about 80% of patients. The remaining cases would require sequence determination but the work load would then be considerably reduced.

In view of the foregoing, validation of the IgVH mutational status determined by L/A ratio and/or ZAP-70 expression can be enhanced by direct determination of the IgVH mutational status by standard sequencing protocols. Additionally, in the event that L/A ratio and ZAP-70 expression give rise to discordant results, it is preferred that the IgVH mutational status be directly determined by standard sequencing protocols. Therefore, the following general method is contemplated for direct determination of the IgVH mutational status by sequencing the IgVH genes:

sequencing the IgVH genes;
comparing the determined IgVH gene sequences to the closest germline counterpart; and
classifying the IgVH gene sequences as:
  mutated if their homology determined by said comparing is less than 98%, or
  unmutated if their homology determined by said comparing is greater than or equal to 98%.

Furthermore the present inventors have developed a simple and inexpensive way to assess simultaneous expression of LPL and ADAM29 by a multiplex RT-PCR technique. Keeping in mind that some cases will appear as doublets (6% of cases) and so will not be informative, the simplicity of the assay should permit that it is performed in most laboratories. In the Examples of the present invention, the present inventors demonstrate that the L/A ratio was at least as performant as the IgVH mutational status in predicting clinical outcome. Thus, this simple determination of LPL and ADAM29 expression would be much more cost effective than Ig sequencing.

To this end, in an embodiment of the present invention, the electrophoretic classification method of IgVH mutational status of a subject having chronic lymphocytic leukemia is conducted by:
  obtaining a sample containing mRNA (preferably a peripheral blood sample, a tissue sample, or extracted B cells from said subject or pre-extracted mRNA) from said subject;
  performing a competitive multiplex PCR assay in the presence of PCR primers for LPL and ADAM29, wherein said PCR primers are SEQ ID NO:3, SEQ ID NO: 4, SEQ ID NO:5, and SEQ ID NO:6,
  separating the PCR amplification product; and
  classifying the IgVH mutational status by determining the relative intensities of the bands corresponding to 410 bp and 445 bp,
  wherein the 410 bp band corresponds to LPL and the 445 bp band corresponds to ADAM29; and
  wherein
    when the intensity of the band at 410 bp is greater than the intensity of the band at 445 bp or when there is only a single band at 410 bp then the IgVH mutational status is classified as being unmutated; and
    when the intensity of the band at 410 bp is less than the intensity of the band at 445 bp or when there is only a single band at 445 bp then the IgVH mutational status is classified as being mutated.

In this embodiment, when a doublet (i.e., bands at 410 bp and 445 bp) is present or when the relative intensities of the band at 410 bp and the band at 445 bp are substantially similar, the present invention contemplates coupling the aforementioned method with direct IgVH mutational status classification by IgVH genes sequencing or quantitative L/A determination (with or without ZAP-70 expression analysis).

The foregoing describes a particular embodiment of the present invention. However, the described method may be performed by using other primers that have been selected for their hybridization to LPL or ADAM29 and, thus, the resultant band's size could be different. In this embodiment, the size of the appropriate primers could varied from 50 to 1000 bp, preferably 50 to 500 bp, more preferably, 75 to 205 bp, depending on the conditions of the hybridization (i.e., stringent conditions), temperature, number of cycles as well as the nature of the buffer. To this end and with the sequence of LPL and ADAM29 provided herein the artisan would be able to readily identify other suitable primers for both genes.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+ 16.6 (log M)+0.41 (% GC)−0.61 (% form)−500/L M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

In view of the foregoing, in another embodiment of the present invention, the electrophoretic classification method of IgVH mutational status of a subject having chronic lymphocytic leukemia is conducted by:

obtaining a sample containing mRNA (preferably a peripheral blood sample, a tissue sample, or extracted B cells from said subject or pre-extracted mRNA) from said subject;

performing a competitive multiplex PCR assay in the presence of PCR primers for LPL and ADAM29, wherein said PCR primers are selected such that the size differences between the bands corresponding to LPL and ADAM29 are resolvable by electrophoresis, separating the PCR amplification product; and classifying the IgVH mutational status by determining the relative intensities of the bands corresponding to LPL and ADAM29, wherein when the intensity of the band corresponding to LPL is greater than the intensity of the band corresponding to ADAM29 or when there is only a single band corresponding to LPL then the IgVH mutational status is classified as being unmutated; and when the intensity of the band corresponding to LPL is less than the intensity of the band corresponding to ADAM29 or when there is only a single band corresponding to ADAM29 then the IgVH mutational status is classified as being mutated.

In addition to their value as surrogate markers, the present inventors evaluated the ability of the L/A ratio and ZAP-70 expression to predict clinical outcome. In univariate analysis, both parameters, as well as the IgVH mutational status, correlated with event free survival (EFS) in the whole population. In multivariate analysis, however, ZAP-70 was no longer selected. For stage A patients, these 3 biological parameters were predictive of EFS. This result is in keeping with Crespo et al.' series where ZAP-70 expression predicted survival only in stage A patients.[20] When considering the stage B and C patients, the L/A ratio was the only parameter which correlated significantly with survival in univariate analysis. The IgVH UM status became a significant risk factor only after adjustment on sex and age in multivariate analysis. In contrast, ZAP-70 expression had no prognostic value in this group of patients. The availability of biological prognostic indicators such as the L/A ratio for stage B and C CLL cases may therefore be of great importance for future risk-adapted treatments.

Prognostics found by using L/A ratio is independent of the Classification of Stage A, B, C and D. L/A ratio is a best prognostic marker of CLL progression than previous stage classification. This conclusion derives from the observation of results shown in Table 8 below.

In yet another embodiment, the present invention provides a method of allowing accurate estimation of the prognosis in a patient having chronic lymphocytic leukemia, by designating the subject as having a significant probability of having an aggressive form of the disease if there is overexpression of the LPL gene or an indolent form of the disease if there is overexpression of ADAM29 gene.

To this end, the present invention provides a method of distinguishing in a subject in need thereof between whether said subject has an aggressive form of chronic lymphocytic leukemia or an indolent form of chronic lymphocytic leukemia comprising obtaining a specimen from said subject;

determining the gene expression levels of LPL and ADAM29 in said specimen;

designating the subject as having a significant probability of having an aggressive form of chronic lymphocytic leukemia if the LPL gene is overexpressed; or an indolent form of chronic lymphocytic leukemia if the ADAM29 gene is overexpressed.

As used herein gene expression of LPL and/or ADAM29 is considered to be overexpressed when expression in the subject is compared to the expression level of the respective gene in a normal "healthy" person. For instance, the absence of LPL expression in normal subjects is well-known. In a preferred embodiment, overexpression is determined on the basis of comparison to a reference (i.e., household gene), for example GAPDH. Using GAPDH, overexpression is considered:

a ratio LPL/GAPDH>1.0 and a ratio of ADAM29/GAPDH>2.8, more prefereably a ratio of ADAM29/GAPDH>3.0.

In summary, the present invention demonstrates that LPL and ADAM29 expression levels correlate with the mutational profile of IgVH genes as well, if not better, than ZAP-70, and is useful to classify the IgVH mutational status of a subject having CLL. Combination of the L/A ratio with ZAP-70 expression provides an accurate prediction of the IgVH mutational status in 80% of CLL cases, thus rendering sequencing unnecessary in these patients. In addition, the L/A ratio is a prognostic indicator which appears to outmatch ZAP-70 in terms of survival prediction for advanced CLL cases.

Also included within the scope of the present invention are kits suitable for detecting (as used herein "detecting" includes "diagnosing and/or prognosing") lymphocytic leukemia (preferably chronic lymphocytic leukemia). Preferably, such a kit would contain primers that hybridize to and/or facilitate amplification of the LPL and/or the ADAM29 genes, and at least one housekeeping gene. Needless-to-say, the present invention contemplates packaging of the present kit such that the primers for the LPL gene and the ADAM29 gene are in the same or different vial (or tube). Also, the housekeeping gene (see above) may admixed with either the LPL gene or the ADAM29 gene or may be in its own independent tube. Additional components that may also be contained in the kit (admixed with one or more of the other components or individually packaged) of the present invention include primers specific for the selected housekeeping gene and reagents (including dNTPs) for amplification. Further, it is to be understood that for each tube used the components therein may be in an aqueous, non-aqueous, dry or crystalline state, or may be admixed with a suitable pharmaceutically acceptable carrier. Wherein the components of the kit are present in a non-aqueous, dry, or crystalline state, it is preferred that the kit further contain an additional vial or tube that contains a suitable diluent, which will provide the user with the appropriate concentration of the components for use in the methods of the present invention. In a preferred embodiment, the kit will contain instructions for using of the components contained in the kit in the methods of the present invention, as included; such instructions can be in the form of printed, electronic, visual, and/or audio instructions.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Materials and Methods

Patients and Samples

A multi-center retrospective study was undertaken on samples from 127 patients diagnosed between October 1979 and February 2003, and identified from the registries of the Pasteur Institute and Hopital Pitie-Salpetriere, Paris, France (n=92), and the University Hospital, Sao Paulo, Brazil (n=35). Inclusion criteria consisted of: 1) diagnosis of typical CLL based on morphologic and phenotypic analyses;[24] 2) availability of frozen samples; 3) previous determination of IgVH mutational status; and 4) patient's informed consent according to Brazilian and French regulations. This series included 87 stage A, 29 stage B and 11 stage C patients according to Binet's staging system[2]. Median follow-up time was 73 months for the whole series (range 1 to 291), while it was 87 months for stage A patients and 50 months for stages B and C. "Progression" was defined as change of clinical stage and/or need for treatment.

As described below, a series of surrogate marker candidates were assessed. Gene expression of LPL, SPG20, ADAM29 and NRIP1 were studied on a first set of 71 patients, including 45 stage A and 26 stage B and C, and compared to the IgVH mutational status taken as the gold standard (described herein below). Only markers showing appropriate test performances in comparison to IgVH mutational status were selected as potential prognosis markers and tested on an additional set of 56 patients.

Only peripheral blood samples were considered for analyses. For 113 patients the peripheral blood samples were acquired at the time of diagnosis. In 14 stage A cases with a very stable lymphocytosis over time, the samples were acquired after a defined time after diagnosis.

Mononuclear cells had been separated by Ficoll-Hypaque gradient centrifugation, and stored in liquid nitrogen. Upon thawing, cell viability was first assessed by trypan blue staining before further analysis. In five cases, B cell populations were purified by negative magnetic selection using anti-CD3, anti-CD14, anti-16 and anti-CD56 monoclonal antibodies (Dynal, Oslo, Norway). Final purity was evaluated by flow cytometry to be greater than 98%. Control samples from 7 healthy adult volunteers were obtained using the same procedures and included peripheral mononuclear blood cells (PBMC, n=4) and purified B cells (n=3). In addition the T-cell line Jurkatt was cultured in RPMI 1640 medium containing 10% fetal calf serum, 2 mM glutamine, 1% sodium pyruvate and penicillin-streptomycin.

IgVH Mutational Status

The IgVH gene sequences were determined as previously described.[25] Briefly, amplification of Ig heavy chain variable regions by PCR was performed on DNA from leukemic cells with consensus primers for the VH framework region 1 and JH genes as previously described[25] or following the BIOMED-2 protocols.[26] Purified PCR products were sequenced either directly or after a cloning procedure using an automated DNA sequencer. Sequence data were analyzed using: (a) IgBLAST available through the website for the National Center for Biotechnology Information, National Library of Medicine, National Institutes of Health (Bethesda, Md., USA) at http://www.ncbi.nlm.nih.gov/igblast, (b) V-BASE available through the website for the Centre for Protein Engineering, Medical Research Council, University of Cambridge (Cambridge, UK) on the web at: mrc-cpe.ca-m.ac.uk/vbase-ok.php?menu=901, and (c) ImMunoGeneTics database available through the website for the The International Immunogenetics Information System (IMGT, Montpellier, France) on the web at: imgt.cines.fr IgVH sequences were considered as mutated if their homology with the closest germline counterpart was less than 98%.

RNA Isolation and cDNA Synthesis

Total cellular RNA was extracted using the RNeasy kit (Qiagen, Courtaboeuf, France) following supplier's instructions. The integrity of RNA was assessed by visualization of the 18S and 28S RNA species upon electrophoresis in agarose gel after ethidium bromide staining. First strand cDNA was synthesized from 2 µg of total RNA, using Superscript II reverse transcriptase (Invitrogen, Cergy-Pontoise, France) and oligodT or random hexamer primers.

Quantitative RT-PCR-

For gene expression analyses of LPL, SPG20, ADAM29 and NRIP1, the present inventors performed RQ-PCR (real-time polymerase chain reaction) using the Light Cycler System (Roche Molecular Biochemicals, Mannheim, Germany) and the SYBR Green I dye. Primers used in this study (Table 1) were designed with the Gene Runner software (Hastings Software, Colorado, USA). RQ-PCR was performed using 100 ng of reversly transcribed total RNA (cDNA) with the following parameters: 10 minutes at 95° C. for initial denaturation, then 40 cycles of 10 seconds at 95° C., 5 seconds at 62° C. and 17 seconds at 72° C.

The specificity of the amplified products was verified by analysis of their respective melting curves as provided by the Light Cycler software. All reactions were performed in duplicate and each PCR run also included the 5 points of the calibration curve and a no-template control. Estimation of the quality of cDNA for each sample was performed by quantification of an endogenous reference, the glyceraldehyde-3-phosphate dehydrogenase (GAPDH). The gene copy number was calculated with a standard curve generated from serially diluted (10-fold dilutions from $10^6$ to $10^2$ copies) plasmids containing the respective sequence (LPL, ADAM29 or Housekeeping gene) verified insert. Results were expressed as the ratio of mean of gene copy number/mean GAPDH copy number×100 (used herein as "normalized gene expression").

Multiplex RT-PCR

The present inventors also evaluated the relative expression of LPL and ADAM29 by multiplex RT-PCR, using the same primers than those for RQ-PCR (Table 1). Different concentrations of primers, MgCl$_2$ and dNTP were first evaluated. Optimized PCR conditions were obtained with primers at the final concentrations of 0.5 µM for LPL and 0.25 µM for ADAM29, 1.5 mM MgCl$_2$ and 200 µM dNTP. Amplifications were performed using 100 ng cDNA and included an initial denaturation step at 94° C. for 5 minutes, followed by 29 cycles of 30 seconds at 95° C., 20 seconds at 62° C. and 30 seconds at 72° C. Finally, the reaction completed with a final elongation step at 72° C. for 5 minutes. PCR products were analyzed on ethidium bromide-stained 2% agarose gel electrophoresis, where they appeared as a 445 bp band for ADAM29 and a 410 bp band for LPL. Amplification of GAPDH was performed in parallel to ensure cDNA integrity.

Alternatively, primers can be fluorescent labeled primers and the resultant PCR products can be analyzed on polyacrylamide gel electrophoresis (GenScan). L/A ration can be determined by measuring and comparing the corresponding surfaces under the curves, after scan.

TABLE 1

Sequences of primers used in RQ-PCR and multiplex-PCR

| Primer | Sequence (5'→3') |
|---|---|
| GAPDH forward | GGTGCTGAGTATGTCGTGGA (SEQ ID NO:1) |
| GAPDH reverse | ATGCCAGTGAGCTTCCGTT (SEQ ID NO:2) |
| LPL forward | GGAATGTATGAGAGTTGGGTGC (SEQ ID NO:3) |
| LPL reverse | CAATGCTTCGACCAGGGGACC (SEQ ID NO:4) |
| ADAM29 forward | TCTTATGTGGGCTGGTGGATCC (SEQ ID NO:5) |
| ADAM29 reverse | GACCTAGATGATGAGCCACTGC (SEQ ID NO:6) |
| SPG20 forward | CTGAAATGTACTGCGGGAGCC (SEQ ID NO:7) |
| SPG20 reverse | CCAACTCACCCAGGAAGCACC (SEQ ID NO:8) |
| NRIP1 forward | GGATAGCACATTACTGGCCTCT (SEQ ID NO:9) |
| NRIP1 reverse | AGGTTTAGGTGAGGTGGCAGG (SEQ ID NO:10) |

Multiparametric Flow Cytometry

Flow-cytometric analysis of ZAP-70 intracellular expression was performed using the method described by Crespo et al.[20] with some minor modifications. Thawed mononuclear cells were fixed in 2% paraformaldehyde and were subsequently permeabilized by incubation with phosphate-buffered saline containing 0.1% saponin (Sigma, Saint-Quentin Favallier, France) and 0.5% bovine serum albumin.

One million cells were first incubated with 2.5 µg of anti-ZAP-70 antibody (clone 2F3.2, Upstate, Lake Placid, N.Y., USA), or irrelevant isotype-matched anti-CD14 monoclonal antibodies (DakoCytomation, Trappes, France). After washing, they were incubated with 1.5 µg of F(ab')$_2$ fluorescein isothiocyanate (FITC)-conjugated goat anti-mouse antibody (Immunotech, Marseille, France). Cells were then washed and incubated with phycoerythrin-cyanin 5 (PC5)-conjugated mouse anti-CD19 (Immunotech), allophycocyanin (APC)-conjugated mouse anti-CD3 and APC-conjugated mouse anti-CD56 (BD Biosciences, San Jose, Calif., USA).

Samples including at least $10^4$ cells were further analysed with a flow cytometer (FACSCalibur, BD Biosciences) and the use of CellQuest Pro software (BD Biosciences). Lymphocyte cells were first selected on size structure characteristics, and then gated on B cells (CD19+, gate R2) and T and NK cells (CD3+CD56+, gate R3). Biparametric dot plot graphs were obtained separately for cells that were stained for respectively CD3, CD56 and ZAP-70, or CD19 and ZAP-70, or CD3, CD56 and CD14 (negative control). In those plots as well as in monoparametric histograms, ZAP-70 expression on CD3+ CD56+ cells served to determine the percentage of CLL cells that were positive for ZAP-70.

Statistical Analyses

Expression levels of the 4 tested genes and of ZAP-70 protein were compared with the IgVH mutational status as a reference. Threshold values that could best discriminate MT from UM cases were first determined by plotting expression values against IgVH percentage of germline homology, and then further refined by calculating Youden's index[27] and validity index (the percentage of correctly classified cases). Thereafter the performance indexes including sensitivity, specificity, positive and negative predictive values were determined.

Distributions of patients, according to Binet staging, sex and IgVH mutational status were compared using Chi square test. Median follow-up was calculated for each Binet stage group.

Since CLL-related deaths were mainly observed in stage B and C (only 4 cases in stage A), while disease progression was the most frequent event for stage A patients, the present inventors evaluated event-free survival, from diagnosis to date of disease progression or CLL-related death or last follow-up visit, for the whole cohort and stage A patients. Overall survival was calculated only for stage B and C patients. Survival analyses were performed using the Kaplan-Meier method. Statistical significance of associations between individual variables and survival was calculated by the log-rank test.

Univariate and multivariate regression analyses were done according to the Cox proportional hazards regression model. As the biological factors studied as potential surrogate markers of IgVH mutational status and prognostic indicators were by definition strongly correlated with IgVH mutational status, it was inappropriate to test them simultaneously by Cox regression. Consequently, two Cox regression analyses were performed: the first one testing IgVH mutational status, the second one testing the other selected factors, in both circumstances with adjustment on age, sex, and when appropriate Binet's staging. Variables with two-tailed P<0.05 were considered as significant. All analyses were done using SPSS Statistical Software, version 11.5 (Chicago, Ill., USA).

Results

Example 1

Patients' Characteristics

Table 2 summarizes the 127 patients' characteristics:

TABLE 2

Clinical and biological characteristics of patients

|  | Stage A | Stage B | Stage C | Stages B + C | Stages A + B + C |
|---|---|---|---|---|---|
| No. Patients | 87 | 29 | 11 | 40 | 127 |
| Age, years* | 63.0 | 58.0 | 59.0 | 58.5 | 61.0 |
| Male sex | 51 (59%) | 24 (83%) | 5 (45%) | 29 (72%) | 80 (63%) |
| Lymphocyte count, $\times 10^9$/L* | 15.2 | 37.2 | 151.8 | 45.0 | 19.0 |
| Hemoglobin, g/dL* | 14.1 | 13.4 | 7.2 | 13.0 | 13.8 |
| Platelets, $\times 10^9$/L* | 212.5 | 160.0 | 187.5 | 172.0 | 198.0 |
| Lymphocyte doubling time |  |  |  |  |  |
| >12 months | 64 (84%) | NA | NA | NA | NA |
| <12 months | 12 (16%) | NA | NA | NA | NA |
| IgVH genes |  |  |  |  |  |
| UM | 27 (31%) | 17 (59%) | 9 (82%) | 26 (65%) | 53 (42%) |
| MT | 60 (69%) | 12 (41%) | 2 (18%) | 14 (35%) | 74 (58%) |
| ZAP-70 |  |  |  |  |  |
| <20% | 45 (65%) | 7 (30%) | 3 (33%) | 10 (31%) | 55 (54%) |
| ≧20% | 24 (35%) | 16 (70%) | 6 (67%) | 22 (69%) | 46 (46%) |
| L/A ratio |  |  |  |  |  |
| <1 | 56 (69%) | 13 (46%) | 2 (20%) | 15 (39%) | 71 (60%) |
| ≧1 | 25 (31%) | 15 (54%) | 8 (80%) | 23 (61%) | 48 (40%) |
| Progression | 22 (25%) | NA | NA | NA | NA |
| CLL-related death | 4 (5%) | 11 (38%) | 6 (55%) | 16 (40%) | 20 (18%) |

*Median values
UM indicates unmutated;
MT, mutated;
L/A, LPL/ADAM29;
NA, not applicable.

Fifty three patients (42%) were allocated to the UM IgVH group while 74 displayed a MT IgVH profile. The MT and UM cases were heterogeneously distributed within Binet stages, since 69% of stage A patients displayed a MT IgVH profile, while 65% were UM among B and C cases (p<0.001). Sex distribution was also heterogeneous with a high proportion of male patients among UM cases (70%) and a slight female predominance (53%) in the MT group (p=0.05). Twenty disease-related deaths were recorded in these series, and 4 additional deaths, unrelated to CLL, occurred among stage A patients. Based on French Cooperative Group guidelines, almost all stage B and C patients received early treatment, whereas treatment was deferred for stage A patients until disease progression. This was the case for 22 stage A patients (25%), of whom 4 died.

Example 2

LPL and ADAM29 are Better Surrogate Markers for IgVH Mutational Status than SPG20 and NRIP1

LPL, SPG20, ADAM29 and NRIP1 were first evaluated in an initial series of 71 patients. The present inventors quantified the expression of these 4 genes on total lymphocytes, since preliminary experiments in five patients showed similar results as compared to purified leukemic cells (data not shown). For each gene, the present inventors determined which expression levels could best segregate UM from MT patients using Youden's and validity indexes. Results showed that overall LPL and ADAM29 performed better than SPG20 and NRIP1 to predict UM and MT IgVH profiles respectively (Table 3). The concordance rate was 83% for ADAM29, 77% for LPL, 65% for SPG20 and 45% for NRIP1.

TABLE 3

Correlation of gene expression with IgVH mutational status

| Gene | LPL | | ADAM29 | | SPG20 | | NRIP1 | | LPL/ADAM29 | |
|---|---|---|---|---|---|---|---|---|---|---|
| expression‡ | ≧1 | <1 | ≧3 | <3 | ≧3.5 | <3.5 | ≧4 | <4 | ≧1 | <1 |
| UM (n = 37) | 30 | 7 | 8 | 29 | 21 | 13 | 17 | 16 | 32 | 5 |
| MT (n = 34) | 9 | 25 | 28 | 6 | 7 | 27 | 19 | 15 | 3 | 31 |
| Sensitivity* | 81% | | 82% | | 57% | | 56% | | 86% | |
| Specificity* | 74% | | 78% | | 79% | | 43% | | 91% | |
| PPV* | 77% | | 78% | | 75% | | 53% | | 91% | |
| NPV* | 78% | | 83% | | 67% | | 52% | | 86% | |

*These parameters were calculated in relation to unmutated IgVH genes for LPL, SPG20, and LPL/ADAM29, and to mutated IgVH genes for ADAM29 and NRIP1.
‡Results were expressed as the ratio of mean of gene copy number/mean GAPDH copy number $\times$ 100
UM indicates unmutated;
MT, mutated;
PPV, positive predictive value;
NPV, negative predictive value.

Next, the present inventors investigated whether a combination of the most discriminating parameters by a simple 1 to 1 LPL/ADAM29 (L/A) ratio could improve their individual predictive potential for mutational status. With a calculated threshold of 1, the L/A ratio displayed better sensitivity and specificity than each marker taken individually. Positive predictive value (PPV) was 91% for UM cases and negative predictive value (NPV) was 86% for MT patients, providing a better performance than each individual marker (Table 3).

Thus the L/A ratio constituted the best marker reflecting the mutational status of IgVH genes in this cohort of 71 CLL patients, with a concordance rate of 89%.

Example 3

Reproducibility of LPL and ADAM29 Quantification

Since LPL and ADAM29 appeared to better reflect the IgVH mutational status, the present inventors evaluated the reproducibility of their quantification by RQ-PCR. This was done by comparing results obtained from replicate samples for 4 patients, 2 overexpressing LPL and 2 overexpressing ADAM29. For each patient, 4 replicates were analyzed during the same reaction run (intra-run variability), and this was repeated on 3 different days (inter-run variability). The overall variability of these 12 replicates is shown in Table 4. Of note, intra-run variability was always smaller than overall variability, with CV being less than 0.5% for LPL and less than 1.1% for ADAM29 (data not shown).

TABLE 4

Reproducibility of RQ-PCR

| Patient | LPL Ct ± SD | LPL CV (%) | ADAM29 Ct ± SD | ADAM29 CV (%) |
|---|---|---|---|---|
| CLL-73 | 23.54 ± 0.46 | 1.97 | NA | NA |
| CLL-105 | 23.96 ± 0.38 | 1.59 | NA | NA |
| CLL-67 | NA | NA | 27.33 ± 1.18 | 4.31 |
| CLL-101 | NA | NA | 23.32 | 2.21 |

Ct indicates threshold cycle;
SD, standard deviation;
CV, coefficient of variation

Example 4

Expression of LPL and ADAM29 in Normal Cells

Although experiments on purified and unpurified CLL cells showed similar results, the present inventors wanted to evaluate a possible expression of LPL and ADAM29 genes in normal cells which might contaminate patient samples. ADAM29 was not detected in PBMC from 4 healthy individuals, nor in purified B cells from 3 additional healthy donors. Similar results were obtained with LPL except for 1 of the 3 purified B cell samples where it was present at low levels (data not shown). In addition the T-cell line Jurkatt failed to express any of these 2 genes. Thus, all or most of the LPL and ADAM29 transcripts that the present inventors measured in patients samples originated from leukemic cells and not from background normal mononuclear cells.

Example 5

L/A Ratio Predicts the IgVH Mutational Status at Least as Well as ZAP-70

Results obtained with the initial CLL series led us to compare LPL and ADAM29 mRNA to ZAP-70 protein expression in the entire cohort of 127 patients, which included the 71 patients studied initially and 56 additional cases. In this series, LPL and ADAM29 values were available for 119 patients, whereas ZAP-70 could be determined for 101 patients and all three parameters for 93 patients. Threshold values were determined and found to be identical to those of the first cohort. On this larger series, the L/A ratio once again provided a better concordance (90%) with IgVH mutational status than LPL (76%) or ADAM29 (82%) taken individually (Table 5).

Figure 1:
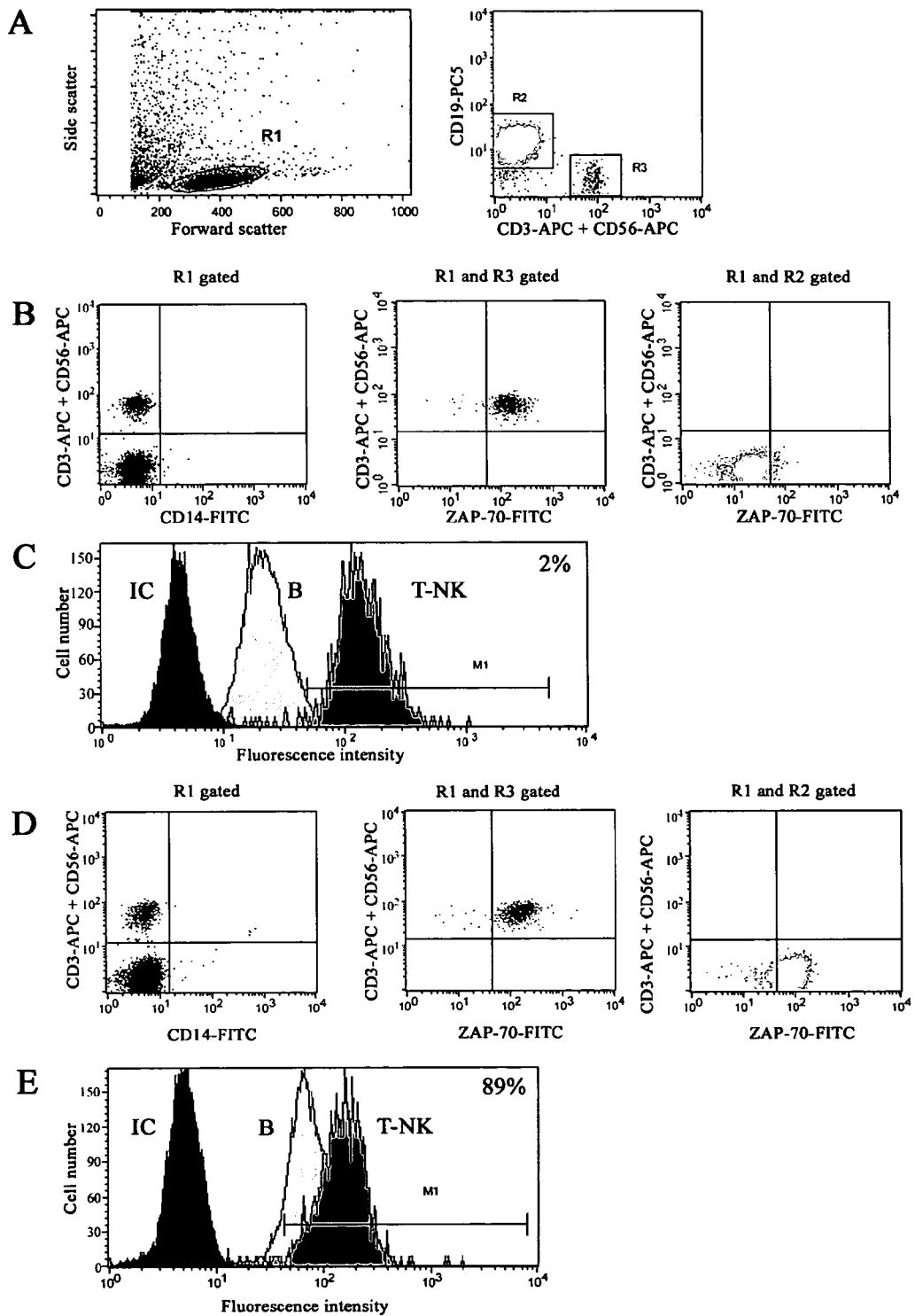
FIG. 1. Flow cytometry analysis of ZAP-70 expression.

ZAP-70 expression was measured by flow cytometry in leukemic B cells in comparison with that of the patients' T and NK cells (FIG. 1). A cut-off value at 20% positivity was found to provide the best correlation with IgVH genes (FIG. 2). Fifty patients (50%) had MT IgVH genes and were ZAP-70 negative while 35 displayed UM IgVH genes (35%) and were ZAP-70 positive. Concordance rate with IgVH mutational status was 84%, thus slightly lower than that obtained with the L/A ratio (Table 5, above).

TABLE 5

Correlation of LPL, ADAM29 gene expression and ZAP-70 protein expression with IgVH mutational status

| Gene expression[‡] | LPL ≥1 | LPL <1 | ADAM29 ≥3 | ADAM29 <3 | LPL/ADAM29 ≥1 | LPL/ADAM29 <1 | ZAP-70 ≥20% | ZAP-70 <20% |
|---|---|---|---|---|---|---|---|---|
| UM | 41 | 9 | 9 | 41 | 43 | 7 | 35 | 5 |
| MT | 19 | 50 | 57 | 12 | 5 | 64 | 11 | 50 |
| Sensitivity* | 82% | | 82% | | 86% | | 87% | |
| Specificity* | 72% | | 83% | | 93% | | 82% | |
| PPV* | 68% | | 77% | | 90% | | 76% | |
| NPV* | 85% | | 86% | | 90% | | 91% | |

LPL and ADAM29 gene expression was quantified by RQ-PCR for 119 patients, while ZAP-70 protein expression was determined by flow cytometry for 101 cases. Abbreviations are explained in Table 3
[‡]Results were expressed as the ratio of mean of gene copy number/mean GAPDH copy number × 100; ZAP-70 is expressed as a percent positivity (see FIG. 2)
*These parameters were calculated in relation to unmutated IgVH genes for LPL and LPL/ADAM29, and to mutated IgVH genes for ADAM29.

Example 6

Combination of ZAP-70 and L/A Ratio Determination Provides Almost Perfect Prediction of IgVH Mutational Status The present inventors next examined the interest of combining ZAP-70 expression and the L/A ratio in the 93 patients for which all 3 parameters had been determined. Cases were scored as "positive" or "negative" for a given marker based on expression values above or below the thresholds. As depicted in Table 6, all double positive patients (ZAP-70$^+$ L/A$^-$; n=30) except one expressed UM IgVH genes, and all double negative cases (ZAP-70$^-$ L/A$^-$; n=44) had MT IgVH genes. Although these clusters demonstrate a strong predictive power, with almost perfect (99%) accuracy, discordant profiles showing only one positive marker still accounted for 20% of CLL patients. They included 13 cases expressing a ZAP-70$^+$ L/A$^-$ profile, whereas 6 patients were ZAP-70$^-$ L/A$^+$. Of note, the mutational status of these 19 cases would have been predicted correctly more often by the L/A ratio alone (13 cases) than by ZAP-70 expression alone (6 cases). The characteristics of these patients are presented in Table 7.

TABLE 6

Groups of CLL patients according to L/A ratio and ZAP-70 expression

| | ZAP-70$^+$ L/A$^+$ | ZAP-70$^+$ L/A$^-$ | ZAP-70$^-$ L/A$^+$ | ZAP-70$^-$ L/A$^-$ |
|---|---|---|---|---|
| UM (n = 37) | 29 | 4 | 4 | 0 |
| MT (n = 56) | 1 | 9 | 2 | 44 |
| Total (n = 93) | 30 (32%) | 13 (14%) | 6 (6%) | 44 (47%) |

Positivity or negativity for ZAP-70 refers to expression values ≥20% or <20% respectively.
Positivity or negativity for L/A ratio refers to expression values ≥1 or <1 respectively.
Abbreviations are explained in Table 2.

TABLE 7

Individual characteristics of the 19 patients presenting discordant results between the L/A ratio and ZAP-70 expression

| Patient | L/A | ZAP-70 (%) | IgV$_H$ (% homology) | Stage | Lymphocytes (×10$^9$/L) | Follow-up (months) | Events |
|---|---|---|---|---|---|---|---|
| UM#1 | <1 | 59 | 1-69 (100) | B | 11 | 91 | Treated |
| UM#2 | <1 | 73 | 3-9 (100) | A | 18.2 | 23 | — |
| UM#3 | <1 | 86 | 1-24 (99) | B | 31.5 | 91 | Treated |
| UM#4 | <1 | 62 | 3-21 (98) | B | 7.8 | 22 | Treated |
| MT#1 | <1 | 40 | 4-34 (93) | A | 11.6 | 251 | — |
| MT#2 | <1 | 62 | 3-7 (94) | A | 8.7 | 153 | — |
| MT#3 | <1 | 81 | 3-21 (94) | B | 8.3 | 100 | Treated |
| MT#4 | <1 | 88 | 3-21 (97) | A | 45.4 | 83 | Treated |
| MT#5 | <1 | 56 | 4-39 (96) | A | 11.8 | 144 | — |
| MT#6 | <1 | 23 | 3-23 (91) | A | 39.7 | 133 | Treated |
| MT#7 | <1 | 82 | 3-13 (97) | B | 34.9 | 54 | Treated |
| MT#8 | <1 | 79 | 3-64 (96) | A | 22.5 | 56 | Treated |
| MT#9 | <1 | 31 | 1-2 (97) | A | 21.8 | 55 | Progression |
| UM#5 | ≧1 | 4 | 3-74 (99) | C | 201.2 | 2 | Dead |
| UM#6 | ≧1 | 7 | 3-21 (100) | A | 12.0 | 24 | — |
| UM#7 | ≧1 | 13 | 3-20 (99) | A | 22.0 | 14 | — |
| UM#8 | ≧1 | 7 | 4-39 (100) | A | 24.0 | 93 | Dead* |
| MT#10 | ≧1 | 3 | 3-23 (95) | B | 74.6 | 15 | Treated |
| MT#11 | ≧1 | 3 | 1-18 (88) | A | 9.6 | 102 | — |

*Death unrelated to CLL
Abbreviations are explained in Table 2.

Example 7

The L/A Ratio is a Predictor of Survival in CLL

Median event free survival (EFS) for the entire cohort was 87 months in CLLs displaying UM IgVH genes as compared to 149 months in MT patients (P<0.0001). It was 84 months for patients with a L/A ratio above 1 and 88 months for patients expressing ZAP-70, while median EFS was not achieved for L/A$^-$ (P<0.0001) nor ZAP-70$^-$ patients (P=0.0001) (FIG. 3A). Multivariate Cox regression showed that, with adjustment on age and sex, UM IgVH and stage B or C were independently associated with disease progression or CLL-related death with hazard ratios of respectively 5.0 (p<0.0001) and 2.6 (p=0.01) (Table 8). Similarly, L/A ratio above 1 and stage B or C were independently and significantly associated with shorter EFS. ZAP-70, however, was not found to be an independent prognosis factor.

In stage A patients, an identical median EFS of 87 months was observed for patients with UM IgVH genes, L/A ratio above 1 and expressing ZAP-70, while it was not achieved for cases with MT IgVH genes, L/A ratio below 1, and ZAP-70 negative (all P<0.0001) (FIG. 3B). In multivariate Cox analyses, after adjustment on age and sex, both ZAP-70 and L/A ratio were independent significant prognostic factors. This was also true for the IgVH mutational status (Table 8).

The 40 stage B and C patients were analyzed together for evaluation of overall survival (OS) (FIG. 3C). There was a trend for longer OS in patients with MT than in those with UM IgVH genes (128 vs 79 months; P=0.067). The L/A ratio was predictive of survival since patients with a ratio above 1 had a median OS of 79 months, while it was not yet reached at time of analysis for those with a ratio below 1 (P=0.03). In contrast ZAP-70 did not correlate with survival in this group (100 vs 80 months; P=0.28). By multivariate Cox analysis, an L/A ratio below 1 was found as a significant prognostic factor, while ZAP-70 was not independently associated with survival. In a separate Cox analysis, IgVH mutational status became a significant prognosis factor, after adjustment on age and sex (Table 8).

TABLE 8

Prognostic factors for disease progression and CLL-related death in multivariate Cox regression

| Factor | Hazard ratio (95% CI) | P |
|---|---|---|
| All stages, event free survival for all stages | | |
| Model 1 including IgVH | | |
| Age | 1.1 (1.0-1.2) | 0.20* |
| Sex (male) | 1.4 (1.0-2.0) | 0.29 |
| Binet's stage B/C | 2.6 (1.8-3.7) | 0.01 |
| Unmutated IgVH | 5.0 (3.4-7.2) | <0.0001 |
| Model 2 including L/A ratio† | | |
| Age | 1.1 (1.0-1.2) | 0.50* |
| Sex (male) | 1.4 (1.2-2.7) | 0.12 |
| Binet's stage B/C | 2.5 (1.7-3.7) | 0.02 |
| L/A ratio ≧1 | 5.6 (3.8-8.1) | <0.0001 |
| Event-free survival for Binet's stage A | | |
| Model 1 including IgVH | | |
| Age | 1.0 (0.9-1.1) | 0.86* |
| Sex | 1.6 (1.0-2.3) | 0.28 |
| Unmutated IgVH | 5.7 (3.6-9.1) | 0.0002 |
| Model 2 including L/A ratio and ZAP-70 | | |
| Age | 0.9 (0.8-1.0) | 0.29* |
| Sex (male) | 1.7 (1.0-2.7) | 0.32 |
| ZAP-70 (<20%) | 4.2 (2.3-7.7) | 0.02 |
| L/A ratio ≧1 | 3.9 (2.1-7.2) | 0.03 |
| Overall survival for stages B and C | | |
| Model 1 including IgVH | | |
| Age | 1.5 (1.2-1.8) | 0.03* |
| Sex (male) | 1.0 (0.5-2.1) | 0.99 |
| Unmutated IgVH | 7.2 (3.4-15.1) | 0.01 |

TABLE 8-continued

Prognostic factors for disease progression and CLL-related death in multivariate Cox regression

| Factor | Hazard ratio (95% CI) | P |
|---|---|---|
| Model 2 including L/A ratio[†] | | |
| Age | 1.6 (1.3-2.0) | 0.05* |
| Sex (male) | 0.5 (0.3-1.3) | 0.46 |
| L/A ratio ≧1 | 6.8 (3.3-14.) | 0.01 |

Multivariate analyses were done separately for IgVH or ZAP-70 and L/A ratio, due to the high concordance between the latter two parameters and the former.
*P-value for trend test
[†]ZAP-70 was not independently associated with disease progression or CLL-related death and was then eliminated in the final Cox model.

Example 8

Determination of the LPL and ADAM29 Gene Expression by a Simple Qualitative Multiplex PCR Assay To simplify the assessment of LPL and ADAM29 gene expression, the present inventors developed a simple competitive multiplex PCR assay, where both genes were simultaneously amplified generating PCR products of different size (respectively 410 bp and 445 bp) (FIG. 4). This assay was then evaluated on 95 patients of our series. Experiments were performed in duplicate on separate PCR for 25 cases and showed a perfect reproducibility.

Using our defined PCR conditions, the results were unambiguous in 89 cases with production of a single band, or 2 bands but with one clearly more intense than the other. They correlated with the RQ-PCR results, since patients expressing LPL preferentially had a L/A ratio above 1, while those expressing ADAM29 predominantly had a L/A ratio below 1. PCR products of both sizes with roughly similar intensities were obtained for 6 patients (6%). In 5 of these 6 cases for whom the multiplex PCR was not conclusive, the L/A ratio values were in the range of 0.7-1.5. None of these genes were detected when tested on purified B cells for healthy individuals or the Jurkatt T-cell line (FIG. 4).

Numerous modifications and variations on the present invention are possible in light of the above teachings. It is, therefore, to be understood that within the scope of the accompanying claims, the invention may be practiced otherwise than as specifically described herein.

REFERENCES

1. Rai K R, Sawitsky A, Cronkite E P, Chanana A D, Levy R N, Pasternack B S. Clinical staging of chronic lymphocytic leukemia. Blood. 1975; 46:219-234

2. Binet J L, Leporrier M, Dighiero G, et al. A clinical staging system for chronic lymphocytic leukemia: prognostic significance. Cancer. 1977; 40:855-864

3. Dighiero G, Maloum K, Desablens B, et al. Chlorambucil in indolent chronic lymphocytic leukemia. French Cooperative Group on Chronic Lymphocytic Leukemia [see comments]. N Engl J Med. 1998; 338:1506-1514

4. Hallek M, Langenmayer I, Nerl C, et al. Elevated thymidine kinase levels identify a subgroup at high risk of disease progression in early, nonsmoldering chronic lymphocytic leukemia. Blood. 1999; 98: 1732-1737

5. Sarfati M, Chevret S, Chastang C, et al. Pronostic importance of serum soluble CD23 level in chronic lymphocytic leukemia. Blood. 1996; 88:4259-4264

6. Magnac C, Porcher R, Davi F, et al. Predictive value of serum thymidine kinase level for Ig-V mutational status in B-CLL. Leukemia. 2003; 17:133-137

7. Montserrat E. Classical and new prognostic factors in chronic lymphocytic leukemia: where to now? Hematol J. 2002; 3:7-9

8. Damle R N, Wasil T, Fais F, et al. Ig V gene mutation status and CD38 expression as novel prognostic indicators in chronic lymphocytic leukemia [see comments]. Blood. 1999; 94:1840-1847

9. Ghia P, Guida G, Stella S, et al. The pattern of CD38 expression defines a distinct subset of chronic lymphocytic leukemia (CLL) patients at risk of disease progression. Blood. 2002

10. Krober A, Seiler T, Benner A, et al. V(H) mutation status, CD38 expression level, genomic aberrations, and survival in chronic lymphocytic leukemia. Blood. 2002; 100: 1410-1416

11. Hamblin T J, Orchard J A, Ibbotson R E, et al. CD38 expression and immunoglobulin variable region mutations are independent prognostic variables in chronic lymphocytic leukemia, but CD38 expression may vary during the course of the disease. Blood. 2002; 99:1023-1029

12. Dohner H, Stilgenbauer S, Benner A, et al. Genomic aberrations and survival in chronic lymphocytic leukemia. N Engl J Med. 2000; 343:1910-1916.

13. Oscier D G, Gardiner A C, Mould S J, et al. Multivariate analysis of prognostic factors in CLL: clinical stage, IGVH gene mutational status, and loss or mutation of the p53 gene are independent prognostic factors. Blood. 2002; 100:1177-1184

14. Schroeder H W, Jr., Dighiero G. The pathogenesis of chronic lymphocytic leukemia: analysis of the antibody repertoire [see comments]. Immunology Today. 1994; 15:288-294

15. Fais F, Ghiotto F, Hashimoto S, et al. Chronic lymphocytic leukemia B cells express restricted sets of mutated and unmutated antigen receptors. J Clin Invest. 1998; 102:1515-1525

16. Hamblin T J, Davis Z, Gardiner A, Oscier D G, Stevenson F K. Unmutated Ig V(H) genes are associated with a more aggressive form of chronic lymphocytic leukemia [see comments]. Blood. 1999; 94:1848-1854

17. Maloum K, Davi F, Merle-Beral H, et al. Expression of unmutated V H genes is a detrimental prognostic factor in chronic lymphocytic leukemia. Blood. 2000; 96:377-379.

18. Rosenwald A, Alizadeh A A, Widhopf G, et al. Relation of gene expression phenotype to immunoglobulin mutation genotype in B cell chronic lymphocytic leukemia. J Exp Med. 2001; 194:1639-1647

19. Wiestner A, Rosenwald A, Barry T S, et al. ZAP-70 expression identifies a chronic lymphocytic leukemia subtype with unmutated immunoglobulin genes, inferior clinical outcome, and distinct gene expression profile. Blood. 2003. 2003; 101:4944-4951

20. Crespo M, Bosch F, Villamor N, et al. ZAP-70 expression as a surrogate for immunoglobulin-variable-region mutations in chronic lymphocytic leukemia. N Engl J Med. 2003; 348:1764-1775

21. Orchard J A, Ibbotson R E, Davis Z, et al. ZAP-70 expression and prognosis in chronic lymphocytic leukaemia. Lancet. 2004; 363:105-111

22. O'Connor S, Starczynski J, Teasdale J, et al. Can Zap-70 protein expression in B-CLL as detected by immunohistochemistry predict VH mutation status?[abstract] Blood. 2003; 102:34a 23. Pittner T, Tschumper R C, Kimlinger T, et al. Expression of ZAP-70 in both unmutated and mutated CLL B cells indicates lack of efficacy as a surrogate marker for immunoglobulin mutational status [abstract]. Blood. 2003; 102:34a 24. Moreau E J, Matutes E, A'Hem R P, et al. Improvement of the chronic lymphocytic leukemia scoring system with the monoclonal antibody SN8 (CD79b). Am J Clin Pathol. 1997; 108:378-382

25. Pritsch O, Troussard X, Magnac C, et al. VH gene usage by family members affected with chronic lymphocytic leukaemia. Br J Haematol. 1999; 107:616-624.

26. van Dongen J J, Langerak A W, Bruggemann M, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. 2003; 17:2257-2317

27. Youden W J. Index of rating diagnostic tests. Cancer. 1950; 3; 32-35

28. Vasconcelos Y, Davi F, Levy V, et al. Binet's staging system and VH genes are independent but complementary prognostic indicators in chronic lymphocytic leukemia. J Clin Oncol. 2003; 21:3928-3932

29. Mead J R, Irvine S A, Ramji D P. Lipoprotein lipase: structure, function, regulation, and role in disease. J Mol Med. 2002; 80:753-769

30. Preiss-Landl K, Zimmermann R, Hammerle G, Zechner R. Lipoprotein lipase: the regulation of tissue specific expression and its role in lipid and energy metabolism. Curr Opin Lipidol. 2002; 13:471-481

31. Murthy V, Julien P, Gagne C. Molecular pathobiology of the human lipoprotein gene. Pharmacol Ther. 1996; 70:101-135

32. de Sanctis J B, Blanca I, Radzioch D, Bianco N E. Lipoprotein lipase expression in natural killer cells and its role in their cytotoxic activity. Immunology. 1994; 83:232-239

33. Yamamoto S, Higuchi S, Yoshiyama K, et al. ADAM family proteins in the immune system. Immunol Today. 1999; 20: 278-284

34. Primakoff P, Myles D G. The ADAM gene family: surface proteins with adhesion and protease activity. Trends Genet. 2000; 16:83-87

35. Cerretti D P, DuBose R F, Black R A, Nelson N. Isolation of two novel metalloproteinase-disintegrin (ADAM) cDNAs that show testis-specific gene expression. Biochem Biophys Res Commun. 1999; 263:810-815

The invention claimed is:

1. A method for determining whether a subject diagnosed as having chronic leukemia has an aggressive form of chronic lymphocytic leukemia or an indolent form of chronic lymphocytic leukemia comprising:
   obtaining a specimen from said subject,
   measuring the gene expression levels of LPL and ADAM29 genes in said specimen, and
   determining a LPL/ADAM29 gene expression ratio, wherein a subject is designated as having: an indolent form of chronic lymphocytic leukemia if the LPL/ADAM29 ratio is less than one, or an aggressive form of chronic lymphocytic leukemia if the LPL/ADAM29 ratio is greater than one.

2. The method according to claim 1, wherein said specimen contains at least one biological material selected from the group consisting of peripheral mononuclear blood cells, a tissue containing B cells, and B cells.

3. The method of claim 1, in which gene expression of the LPL and ADAM29 genes is determined by RT-PCR.

4. A method for prognosing event-free survival (EFS) or overall survival (OS), or both, in a subject having chronic lymphocytic leukaemia comprising:
   obtaining a specimen from a subject;
   determining the gene expression levels of the LPL and ADAM29 genes in the specimen;
   determining the LPL/ADAM29 gene expression ratio;
   prognosing the subject as having a significant probability of event-free survival or overall survival when the LPL/ADAM29 ratio is less than one; or
   prognosing the subject as having a significant probability of a shorter event-free survival or overall survival when the LPL/ADAM29 ratio is greater than or equal to one.

5. The method of claim 4, wherein the subject is determined to have an LPL/ADAM29 ratio of less than one and is diagnosed as having an indolent form of chronic lymphocytic leukaemia characterized by greater event-free survival or greater overall survival than an aggressive form of chronic lymphocytic leukaemia.

6. The method of claim 4, wherein the subject is determined to have an LPL/ADAM29 ratio of one or more and is diagnosed as having an aggressive form of chronic lymphocytic leukaemia characterized by shorter event-free survival or shorter overall survival than an indolent form of chronic lymphocytic leukaemia.

* * * * *